(12) United States Patent
Achrol et al.

(10) Patent No.: US 8,790,916 B2
(45) Date of Patent: Jul. 29, 2014

(54) MICROFLUIDIC METHOD AND SYSTEM FOR ISOLATING PARTICLES FROM BIOLOGICAL FLUID

(75) Inventors: Achal Singh Achrol, Menlo Park, CA (US); Palaniappan Sethu, Louisville, KY (US)

(73) Assignee: GeneStream, Inc., Menlo Park, CA (US)

( * ) Notice: Subject to any disclaimer, the term of this patent is extended or adjusted under 35 U.S.C. 154(b) by 655 days.

(21) Appl. No.: 12/779,746

(22) Filed: May 13, 2010

(65) Prior Publication Data

US 2011/0020459 A1    Jan. 27, 2011

Related U.S. Application Data

(60) Provisional application No. 61/178,429, filed on May 14, 2009.

(51) Int. Cl.
| | | |
|---|---|---|
| C12M 1/34 | (2006.01) | |
| G01N 27/74 | (2006.01) | |
| A61K 35/12 | (2006.01) | |

(52) U.S. Cl.
CPC .......... *G01N 27/745* (2013.01); *B03C 2201/18* (2013.01); *B01L 2300/0883* (2013.01); *A61K 35/12* (2013.01)
USPC .......................... 435/287.1; 436/526; 422/414

(58) Field of Classification Search
None
See application file for complete search history.

(56) References Cited

U.S. PATENT DOCUMENTS

| | | | |
|---|---|---|---|
| 4,795,698 A | | 1/1989 | Owen et al. |
| 4,847,209 A | * | 7/1989 | Lewis et al. .................. 436/533 |
| 4,859,582 A | | 8/1989 | Stryer et al. |
| 4,910,148 A | | 3/1990 | Sorensen et al. |
| 4,925,788 A | | 5/1990 | Liberti |
| 5,022,980 A | | 6/1991 | Tanaka et al. |
| 5,055,556 A | | 10/1991 | Stryer et al. |
| 5,096,669 A | | 3/1992 | Lauks et al. |
| 5,108,933 A | | 4/1992 | Liberti et al. |
| 5,186,827 A | | 2/1993 | Liberti et al. |
| 5,200,084 A | | 4/1993 | Liberti et al. |
| 5,385,707 A | | 1/1995 | Miltenyi et al. |
| 5,411,863 A | | 5/1995 | Miltenyi |
| 5,429,927 A | | 7/1995 | Afseth et al. |
| 5,466,574 A | | 11/1995 | Liberti et al. |
| 5,512,332 A | | 4/1996 | Liberti et al. |
| 5,512,439 A | | 4/1996 | Hornes et al. |

(Continued)

FOREIGN PATENT DOCUMENTS

GB    WO 2008/155519    * 12/2008 ................ B01L 3/00

*Primary Examiner* — Chris L Chin
*Assistant Examiner* — Richard Moerschell
(74) *Attorney, Agent, or Firm* — Jeffrey Schox

(57) ABSTRACT

The invention relates to a system and method for isolating particles from a biological fluid, including: obtaining a sample of biological fluid from a source (e.g. a patient) in which the sample contains particles of multiple sample particle types; tagging particles in the sample with tagging agents, including mixing the sample with a solution of magnetic tagging agents that selectively bind to particles of at least one of the sample particle types, thereby forming a group of tagged particles in the sample; passing the sample through a magnetic conduit having a magnetic field that interacts with at least some of the tagged particles; sorting the particles of the sample into multiple groups based on the interaction between the tagged particles and the magnetic field; and optionally returning selected portions of the processed fluid back to its source with or without the addition of appropriate therapeutic agents.

21 Claims, 11 Drawing Sheets

(56) References Cited

U.S. PATENT DOCUMENTS

| | | |
|---|---|---|
| 5,525,493 A | 6/1996 | Hornes et al. |
| 5,541,072 A | 7/1996 | Wang et al. |
| 5,543,289 A | 8/1996 | Miltenyi |
| 5,597,531 A | 1/1997 | Liberti et al. |
| 5,622,831 A | 4/1997 | Liberti et al. |
| 5,637,469 A | 6/1997 | Wilding et al. |
| 5,646,001 A | 7/1997 | Terstappen et al. |
| 5,660,990 A | 8/1997 | Rao et al. |
| 5,691,208 A | 11/1997 | Miltenyi et al. |
| 5,693,539 A | 12/1997 | Miltenyi et al. |
| 5,698,271 A | 12/1997 | Liberti et al. |
| 5,705,059 A | 1/1998 | Miltenyi |
| 5,711,871 A | 1/1998 | Miltenyi |
| 5,741,714 A | 4/1998 | Liberti |
| 5,759,820 A | 6/1998 | Hornes et al. |
| 5,779,892 A | 7/1998 | Miltenyi et al. |
| 5,786,161 A | 7/1998 | Irsch et al. |
| 5,795,470 A | 8/1998 | Wang et al. |
| 5,842,787 A | 12/1998 | Kopf-Sill et al. |
| 5,866,099 A | 2/1999 | Owen et al. |
| 5,876,593 A | 3/1999 | Liberti et al. |
| 5,919,135 A * | 7/1999 | Lemelson ............... 600/407 |
| 5,942,443 A | 8/1999 | Parce et al. |
| 5,957,579 A | 9/1999 | Kopf-Sill et al. |
| 5,985,153 A | 11/1999 | Dolan et al. |
| 5,993,665 A | 11/1999 | Terstappen et al. |
| 5,994,517 A | 11/1999 | Ts et al. |
| 6,013,188 A | 1/2000 | Terstappen et al. |
| 6,013,532 A | 1/2000 | Liberti et al. |
| 6,020,210 A | 2/2000 | Miltenyi |
| 6,120,856 A | 9/2000 | Liberti et al. |
| 6,132,607 A * | 10/2000 | Chen et al. ............... 210/208 |
| 6,136,182 A | 10/2000 | Dolan et al. |
| 6,186,660 B1 | 2/2001 | Kopf-Sill et al. |
| 6,228,624 B1 | 5/2001 | Terstappen |
| 6,361,749 B1 | 3/2002 | Terstappen et al. |
| 6,365,362 B1 | 4/2002 | Terstappen et al. |
| 6,417,011 B1 | 7/2002 | Miltenyi |
| 6,432,630 B1 | 8/2002 | Blankenstein |
| 6,444,461 B1 | 9/2002 | Knapp et al. |
| 6,468,432 B1 | 10/2002 | Miltenyi et al. |
| 6,471,860 B1 | 10/2002 | Miltenyi et al. |
| 6,479,299 B1 | 11/2002 | Parce et al. |
| 6,482,592 B1 | 11/2002 | Lundeberg et al. |
| 6,517,234 B1 | 2/2003 | Kopf-Sill et al. |
| 6,551,843 B1 | 4/2003 | Rao et al. |
| 6,558,944 B1 | 5/2003 | Parce et al. |
| 6,576,428 B1 | 6/2003 | Assenmacher et al. |
| 6,602,422 B1 | 8/2003 | Miltenyi et al. |
| 6,613,581 B1 | 9/2003 | Wada et al. |
| 6,620,627 B1 | 9/2003 | Liberti et al. |
| 6,623,982 B1 | 9/2003 | Liberti et al. |
| 6,623,983 B1 | 9/2003 | Terstappen et al. |
| 6,637,463 B1 * | 10/2003 | Lei et al. ............... 137/803 |
| 6,645,731 B2 | 11/2003 | Terstappen et al. |
| 6,660,159 B1 | 12/2003 | Terstappen et al. |
| 6,675,878 B2 | 1/2004 | Haasch et al. |
| 6,733,645 B1 | 5/2004 | Chow |
| 6,787,233 B1 | 9/2004 | Molteberg et al. |
| 6,790,366 B2 | 9/2004 | Terstappen et al. |
| 6,830,886 B1 | 12/2004 | Bosio et al. |
| 6,861,259 B2 | 3/2005 | Columbus |
| 6,890,426 B2 | 5/2005 | Terstappen et al. |
| 6,906,182 B2 | 6/2005 | Ts et al. |
| 6,960,449 B2 | 11/2005 | Wang et al. |
| 6,984,702 B2 | 1/2006 | Fonnum et al. |
| 6,986,913 B2 | 1/2006 | Fonnum et al. |
| 7,011,794 B2 | 3/2006 | Kagan et al. |
| 7,030,228 B1 | 4/2006 | Schmitz et al. |
| 7,056,657 B2 | 6/2006 | Terstappen et al. |
| 7,067,263 B2 | 6/2006 | Parce et al. |
| 7,091,048 B2 | 8/2006 | Parce et al. |
| 7,118,910 B2 | 10/2006 | Unger et al. |
| 7,119,248 B1 | 10/2006 | Rajewsky et al. |
| 7,138,269 B2 | 11/2006 | Blankenstein |
| 7,160,707 B2 | 1/2007 | Fonnum et al. |
| 7,166,423 B1 | 1/2007 | Miltenyi et al. |
| 7,173,124 B2 | 2/2007 | Deggerdal et al. |
| 7,195,986 B1 | 3/2007 | Bousse et al. |
| 7,217,762 B1 | 5/2007 | Joergedal et al. |
| 7,262,177 B2 | 8/2007 | Ts et al. |
| 7,267,950 B2 | 9/2007 | Belly et al. |
| 7,282,180 B2 | 10/2007 | Tibbe et al. |
| 7,282,350 B2 | 10/2007 | Rao et al. |
| 7,285,411 B1 | 10/2007 | Parce et al. |
| 7,291,497 B2 | 11/2007 | Holmes et al. |
| 7,306,910 B2 | 12/2007 | Wang |
| 7,312,085 B2 | 12/2007 | Chou et al. |
| 7,332,288 B2 | 2/2008 | Terstappen et al. |
| 7,348,142 B2 | 3/2008 | Wang |
| 7,373,778 B2 | 5/2008 | Bunker et al. |
| 7,378,279 B2 | 5/2008 | Bosio |
| 7,387,715 B2 | 6/2008 | Vogel et al. |
| 7,452,726 B2 | 11/2008 | Chou et al. |
| 7,473,526 B2 | 1/2009 | Wang |
| 7,476,363 B2 | 1/2009 | Unger et al. |
| 7,604,777 B2 | 10/2009 | Columbus |
| 7,604,965 B2 | 10/2009 | Mcbride et al. |
| 7,635,594 B2 | 12/2009 | Holmes et al. |
| 7,659,084 B2 | 2/2010 | Frentsch et al. |
| 7,666,308 B2 | 2/2010 | Scholtens et al. |
| 7,666,361 B2 | 2/2010 | Mcbride et al. |
| 7,670,559 B2 | 3/2010 | Chien et al. |
| 7,691,333 B2 | 4/2010 | Mcbride et al. |
| 7,695,956 B2 | 4/2010 | Tsinberg et al. |
| 7,749,737 B2 | 7/2010 | Mcbride et al. |
| 7,754,150 B2 | 7/2010 | Wada et al. |
| 7,758,737 B1 | 7/2010 | Chow |
| 7,763,689 B2 | 7/2010 | Fonnum et al. |
| 7,764,821 B2 | 7/2010 | Coumans et al. |
| 7,777,885 B2 | 8/2010 | Coumans et al. |
| 7,790,116 B2 | 9/2010 | Bousse et al. |
| 7,815,863 B2 | 10/2010 | Kagan et al. |
| 7,820,427 B2 | 10/2010 | Unger et al. |
| 7,828,968 B2 | 11/2010 | Tibbe et al. |
| 7,837,946 B2 | 11/2010 | Mcbride et al. |
| 7,863,012 B2 | 1/2011 | Rao et al. |
| 7,864,927 B2 | 1/2011 | Loizeaux |
| 7,867,454 B2 | 1/2011 | Goodsaid et al. |
| 7,888,125 B2 | 2/2011 | Gibbons et al. |
| 7,901,950 B2 | 3/2011 | Connelly et al. |
| 7,927,805 B2 | 4/2011 | Raponi et al. |
| 7,932,036 B1 | 4/2011 | Raponi et al. |
| 7,943,397 B2 | 5/2011 | Tibbe et al. |
| 7,985,340 B2 | 7/2011 | Almaasbak et al. |
| 7,989,614 B2 | 8/2011 | Deggerdal et al. |
| 8,007,740 B2 | 8/2011 | Liu et al. |
| 8,007,999 B2 | 8/2011 | Holmes et al. |
| 8,008,032 B2 | 8/2011 | Forsyth et al. |
| 8,008,034 B2 | 8/2011 | Gibbons et al. |
| 8,012,744 B2 | 9/2011 | Gibbons et al. |
| 8,038,987 B2 | 10/2011 | Fonnum et al. |
| 8,088,593 B2 | 1/2012 | Burd et al. |
| 8,101,402 B2 | 1/2012 | Holmes |
| 8,110,101 B2 | 2/2012 | Tibbe et al. |
| 8,110,351 B2 | 2/2012 | Bosnes |
| 8,128,890 B2 | 3/2012 | Droog et al. |
| 8,129,126 B2 | 3/2012 | Thiel et al. |
| 8,157,434 B2 | 4/2012 | Cohen et al. |
| 8,158,405 B2 | 4/2012 | Boyette et al. |
| 8,158,430 B1 | 4/2012 | Roy et al. |
| 8,183,039 B2 | 5/2012 | Schmitz et al. |
| 8,183,353 B2 | 5/2012 | Wang |
| 8,189,899 B2 | 5/2012 | Coumans et al. |
| 2002/0006670 A1 * | 1/2002 | Wu et al. ............... 436/514 |
| 2003/0022249 A1 | 1/2003 | Schmitz et al. |
| 2004/0229293 A1 | 11/2004 | Chan-Hui et al. |
| 2005/0021235 A1 * | 1/2005 | Bar-Or et al. ............... 702/19 |
| 2005/0053952 A1 | 3/2005 | Hong et al. |
| 2005/0056313 A1 | 3/2005 | Hagen et al. |
| 2005/0129580 A1 * | 6/2005 | Swinehart et al. ............... 422/100 |
| 2005/0214832 A1 * | 9/2005 | Haemmerle et al. ............... 435/6 |
| 2005/0239152 A1 * | 10/2005 | Irth et al. ............... 435/8 |
| 2006/0081954 A1 * | 4/2006 | Tondra et al. ............... 257/421 |

(56) References Cited

U.S. PATENT DOCUMENTS

| | | |
|---|---|---|
| 2006/0134599 A1 | 6/2006 | Toner |
| 2007/0031283 A1 | 2/2007 | Davis et al. |
| 2007/0059680 A1 | 3/2007 | Kapur et al. |
| 2007/0059781 A1 | 3/2007 | Kapur et al. |
| 2007/0092876 A1 | 4/2007 | Xu |
| 2007/0122819 A1 | 5/2007 | Wu et al. |
| 2007/0172899 A1 | 7/2007 | Graham et al. |
| 2007/0172903 A1 | 7/2007 | Toner |
| 2007/0207548 A1 | 9/2007 | Blankenstein |
| 2007/0231851 A1 | 10/2007 | Toner |
| 2007/0259424 A1 | 11/2007 | Toner |
| 2007/0264675 A1 | 11/2007 | Toner |
| 2008/0003689 A1 | 1/2008 | Lee et al. |
| 2008/0176211 A1 | 7/2008 | Spence et al. |
| 2008/0181828 A1* | 7/2008 | Kluck .......................... 422/128 |
| 2008/0269163 A1 | 10/2008 | Sostaric et al. |
| 2009/0087925 A1 | 4/2009 | Wagner et al. |
| 2009/0136982 A1 | 5/2009 | Tang |
| 2009/0194420 A1 | 8/2009 | Mariella et al. |
| 2009/0288479 A1* | 11/2009 | Woody et al. .................. 73/105 |
| 2010/0003666 A1 | 1/2010 | Lee et al. |
| 2010/0044232 A1 | 2/2010 | Lin et al. |
| 2010/0069815 A1 | 3/2010 | Sohka et al. |
| 2010/0081144 A1 | 4/2010 | Holmes |
| 2010/0093052 A1 | 4/2010 | Chalmers et al. |
| 2011/0027901 A1 | 2/2011 | Gaster et al. |

* cited by examiner

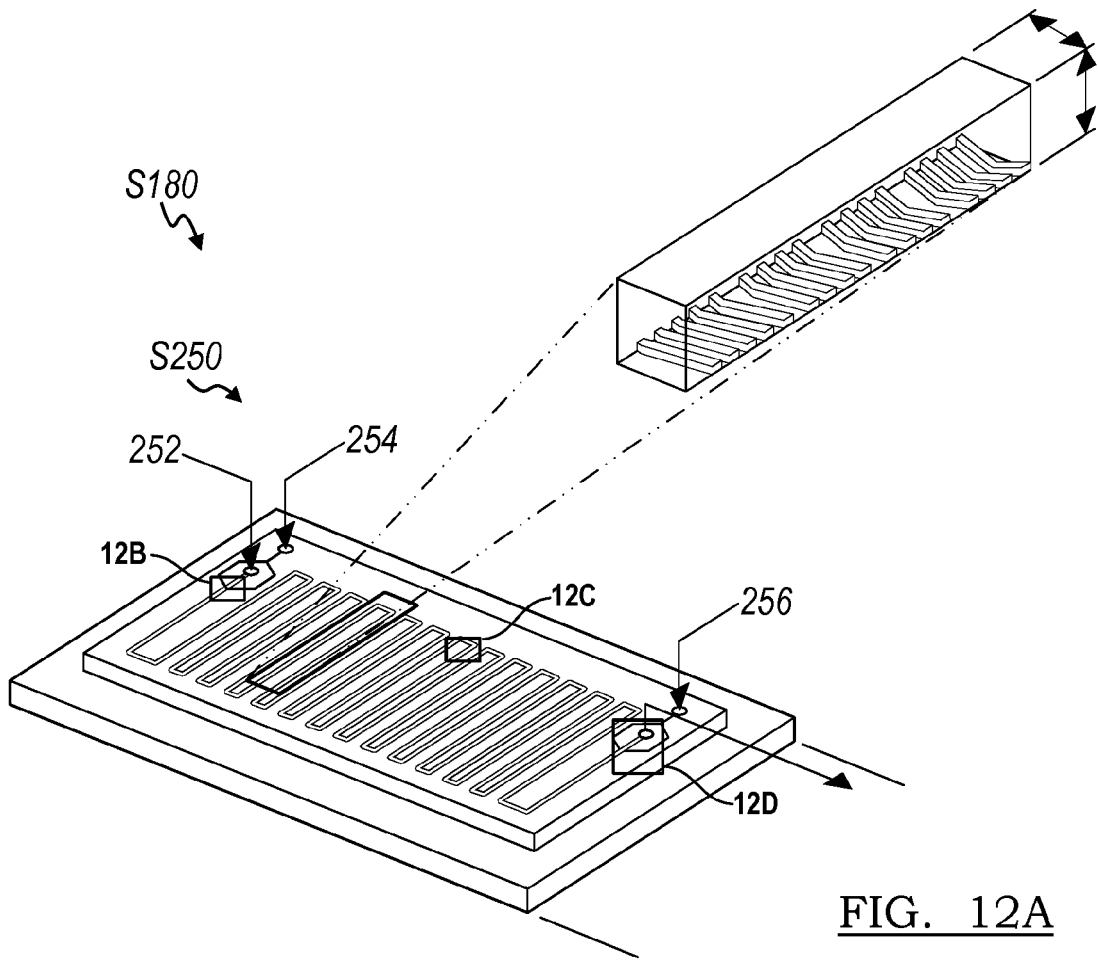
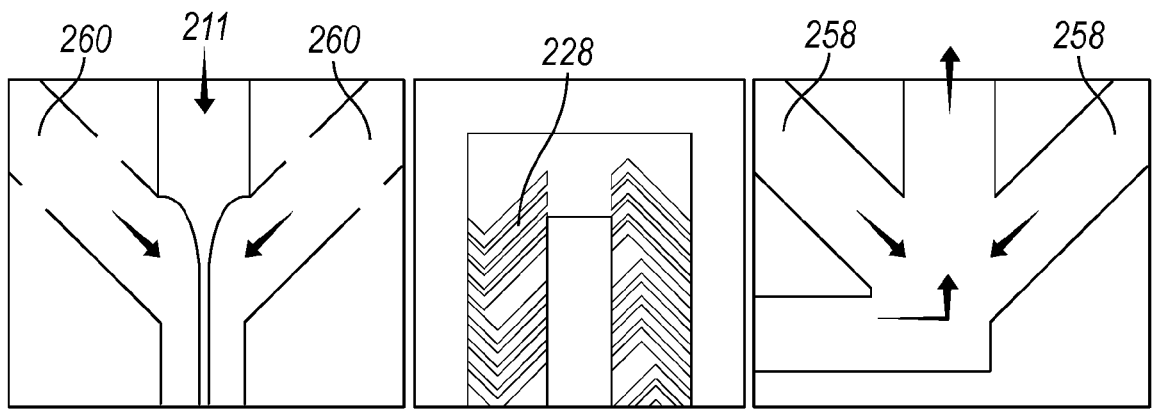
FIG. 12A
FIG. 12B
FIG. 12C
FIG. 12D

MICROFLUIDIC METHOD AND SYSTEM FOR ISOLATING PARTICLES FROM BIOLOGICAL FLUID

CROSS-REFERENCE TO RELATED APPLICATIONS

This application claims the benefit of U.S. Provisional Application No. 61/178,429, filed 14 May 2009, and which is incorporated in its entirety by this reference.

TECHNICAL FIELD

This invention relates generally to biological tissue analysis in the fields of medical diagnosis, dialysis and drug delivery. More specifically, it relates to an improved microfluidic system and method for isolating particles from biological fluid at the point-of-care.

BACKGROUND

It is useful to isolate one or more particular types of particles in a biological fluid sample in an automated fashion at the point-of-care in many applications of healthcare and medical research, such as sample analysis for diagnosis and monitoring purposes. These particles include cells, proteins, nucleic acids and other molecules commonly found in biological fluid. In one example, early detection of tumor cells circulating in the blood of a cancer-afflicted patient may help alert clinicians to tumor progression before the cancer metastasizes and spreads to other parts of the body, and could provide a surrogate marker for monitoring successful treatment response. In another example, detection of circulating endothelial cells and endothelial progenitor cells may help clinicians monitor new blood vessel formation in both normal processes (e.g. wound healing, revascularization after cerebral ischemia or myocardial infarction) and abnormal pathological processes (e.g. tumor growth, vascular malformations).

There are several conventional setups used for particle isolation from biological fluids. However, conventional particle isolation systems are slow and inefficient, cannot be done in an automated fashion at the patient bedside, and result in outputs that are less pure and lead to inaccurate analyses. Conventional particle isolation systems are also limited in their ability to isolate rare particle populations (e.g. rare cells and proteins) from complex fluid tissue samples. For example, immuno-modified magnetic nanoparticle (nanobead)-based separation, which selectively isolates phenotypically identical cells based on their affinity and binding to specific antibodies and/or a magnetic field, is not suitable for detection or isolation of rare cells such as tumor cells due to its poor efficiency. Problems related to efficiency and purity can be attributed to analyzing samples with a non-uniform distribution of particles during particle isolation, poor labeling with immuno-modified nanobeads, a non-uniform magnetic field within a macroscale test tube or container during magnetic enrichment, and an inability to process samples in a continuous flow through format. Conventional setups that are slow, less efficient, and result in less pure samples limit accuracy of resulting analysis of isolated cells, and limits the throughput and number of target rare cells that can be isolated.

Isolation of particles from biological fluids is also at the core of medical treatment using dialysis systems, which process biological fluids with semipermeable membranes that filter substances from the fluid prior to recirculation back to its source. These systems suffer from the nonselective nature of semipermeable membranes and the inability to target specific particles for removal. As such, there is a demand for a point-of-care device in which the system is capable of selectively removing specific particles from the biological fluid, while returning the remaining processed fluid back to its source.

Thus, there is a need in the medical field to create an improved system and method for isolating particles from biological fluid at the point-of-care. This invention provides such an improved system and method.

BRIEF DESCRIPTION OF THE FIGURES

FIGS. 12A and 12B-12D are perspective and detailed schematic views, respectively, of the lytic conduit of the system of a preferred embodiment;

DESCRIPTION OF THE PREFERRED EMBODIMENTS

The following description of preferred embodiments and examples of the invention is not intended to limit the invention to these preferred embodiments and examples, but rather to enable any person skilled in the art to make and use this invention.

1. Method for Isolating Particles

Figure 1:
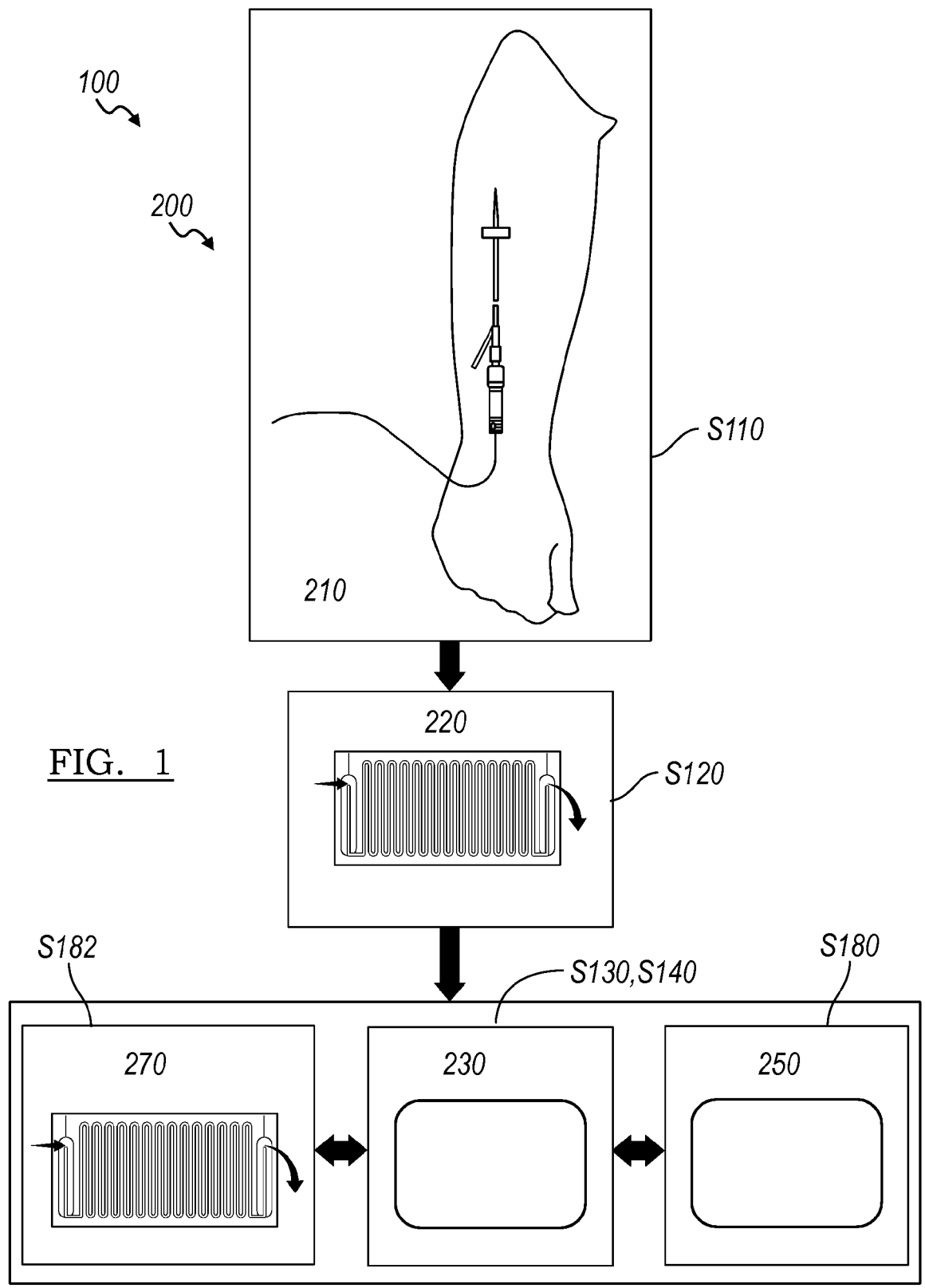
FIG. 1 is a flowchart schematic of the system of a preferred embodiment.

As shown in FIG. 1, the method of a preferred embodiment for isolating particles preferably includes obtaining a sample of biological fluid S110 directly from a cannula inserted in the patient, in which the sample contains particles of multiple sample particle types; tagging particles in the sample S120 with tagging agents, including mixing a solution of magnetic tagging agents that selectively bind to particles of at least one of the sample particle types, thereby forming a group of tagged particles and another group of untagged particles within the sample; passing the sample through a magnetic conduit S130 having a magnetic field that interacts with at least a portion of the tagged particles; and sorting the particles of the sample S140 into at least two groups based on the interaction between the tagged particles and the magnetic field. In some embodiments, the method may additionally and/or alternatively include mixing at least some of the sample with a lytic solution S182 that selectively lyses sample particles, and/or passing the sample through an immunoaffinity capture chamber S180 that selectively captures sample particles for particle depletion in the sample. In some embodiments, the method may additionally and/or alternatively include returning at least a portion of the sample to the patient for recirculation in the body of the patient, and/or adding a therapeutic agent from one or more reservoirs to the returning portion of the sample.

The method preferably isolates specific particle populations from bodily fluids such as peripheral blood, cord blood, urine, cerebrospinal fluid, bone marrow aspirates, homogenized tissue, saliva, and lymph, but may isolate particles from any suitable fluid, such as for diagnostic and therapeutic applications. The specific particle populations in the sample are preferably cells such as specific leukocyte subpopulations and immune cells, circulating tumor cells (CTCs), circulating endothelial cells (ECs), circulating endothelial progenitor cells (EPCs), and/or various circulating stem cells. Alternatively, the method may be used to isolate proteins, nucleic acids, and/or any suitable particle of interest in the biological fluid. Specific examples of suitable applications of the method include: isolating EPCs and circulating stem cells for therapeutic and diagnostic uses; analyzing cell gene expression and/or characterizing activation of cells via presence of phosphorylated intracellular signaling molecules; monitoring immune cell activation and response to certain pharmacotherapies; characterizing ECs and EPCs as markers for blood vessel growth; and characterizing CTCs to determine risk of metastasis and treatment choice, but the method may be used in any suitable application. The method is preferably performed at the point-of-care for clinical purposes including prognosis, diagnosis, and/or patient monitoring, but may be performed in a research and/or laboratory environment to enable clinician-scientists to process samples at the point-of-care in clinical trials and research. In some embodiments of the method in which at least some of the sample is returned to the patient for recirculation in the body of the patient, the method selectively isolates and removes specific particles from the sample of biological fluid, while returning the remaining processed fluid back to the body. In one example, certain immune cells and secreted cytokines play a role in the pathogenesis of sepsis, and selective removal of these particles from circulating blood may help prevent the development of sepsis in at-risk, critically ill patients. Furthermore, in some embodiments of the method, adding a therapeutic agent to the returning fluid helps treat the patient by, for example, controlling administration of therapeutic agents on the basis of detected levels of particles present in the biological fluid. In one example, systemic or localized delivery of chemotherapeutic agents from one or more reservoirs could be controlled on the basis of detection of particles such as circulating tumor cells and/or tumor antigens. In another example, systemic delivery of immune modifying drugs from one or more reservoirs in the treatment of autoimmune disease, sepsis or infection could be controlled on the basis of detection of particles such as activated immune cells and/or high levels of secreted cytokines.

Figure 2:
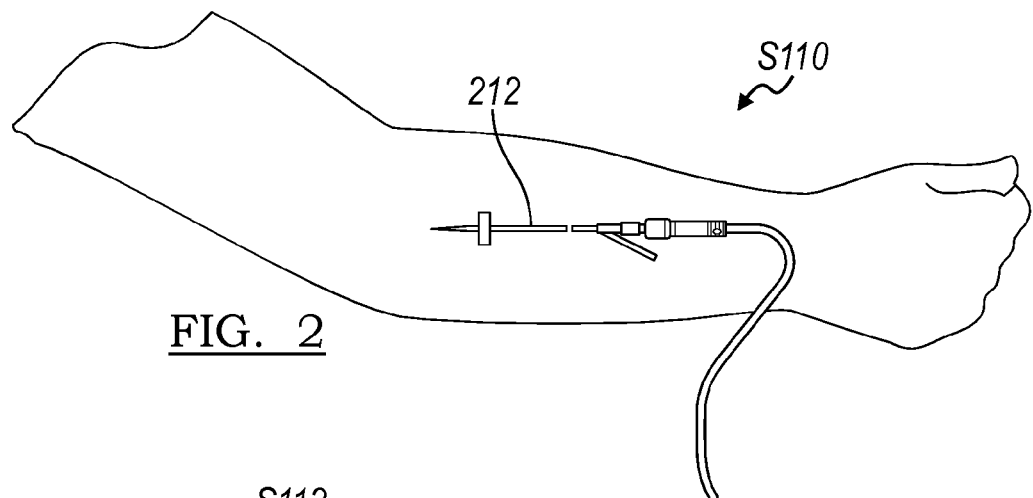
FIG. 2 is a schematic of the sampling module.

The step of obtaining a sample S110 functions to receive a sample of biological fluid from the patient for analytical purposes. The sample may be blood, cerebrospinal fluid, or urine, or any suitable bodily fluid. As shown in FIG. 2, obtaining a sample preferably includes receiving fluid from a catheter, needle, or any suitable cannula at the point-of-care of the patient, such as at bedside during in-patient care or the out-patient setting in patients with in-dwelling catheters or other cannulas. For example, a blood sample may be obtained through an arterial line, an intravenous line, a peripherally inserted central catheter, or a central line. As another example, a cerebrospinal fluid sample may be obtained through an external ventricular drain or a lumbar drain. As another example, a urine sample may be obtained through a Foley catheter or a suprapubic catheter. The process of sample collection from catheter or cannula to the microfluidic device can be further assisted by use of vacuum tubing and/or roller mechanisms that facilitate movement of the fluid through the catheter system rapidly to the microfluidic device. These and other fluid extraction methods are well known in the art, and any suitable method of obtaining bodily fluid may be performed. The sample is preferably heterogeneous in that it preferably includes particles of multiple sample particle types. For instance, a blood sample typically includes more populous cell types like erythrocytes and leukocytes, and may include rarer cell types like CTCs. Each sample particle type may further be classified as a targeted particle that is of interest or an untargeted particle that is not of interest, and its classification preferably depends on the specific application of the method.

The step of obtaining a sample preferably further includes obtaining a uniform distribution of particles in the sample. As shown in FIG. 3, obtaining a uniform distribution may include perturbing with a rocker mechanism S112 that continuously, gently agitates the sample, with a rotating mechanism that continuously, gently turns the sample S114 against gravity like a cement truck, or any suitable mechanism that shifts the sample enough to prevent sedimentation of cells in the sample and helps ensure a uniform particle distribution in the sample.

Figure 4:
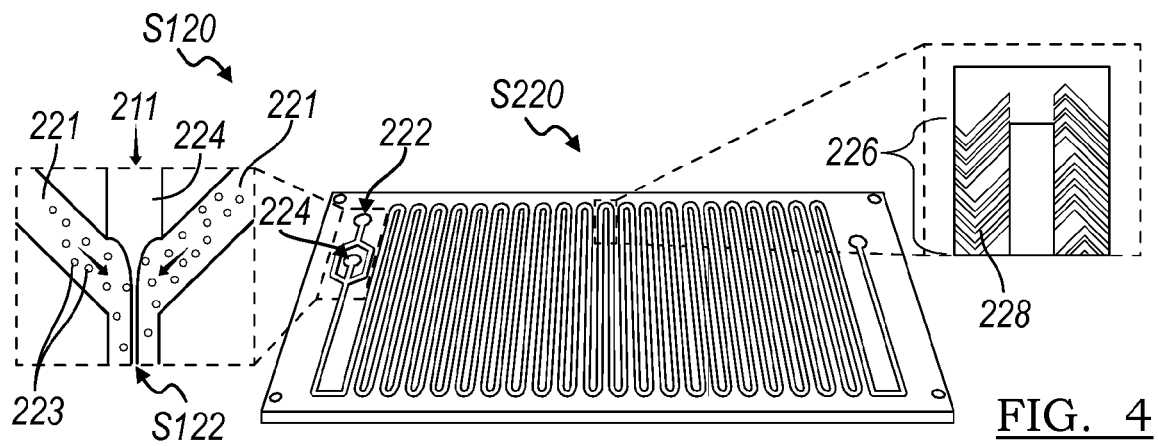
FIG. 4 is a schematic of the tagging conduit of the system of a preferred embodiment.

The step of tagging particles in the sample with tagging agents S120 functions to selectively tag particles with tagging agents that selectively bind to particles in the sample. The tagging agents may bind to and label targeted particles, but may additionally and/or alternatively bind to and label untargeted particles. As shown in FIG. 4, the step of tagging particles preferably includes mixing the sample with a solution of tagging agents S122 in a tagging conduit and allowing unbound tagging agents to exit the tagging conduit. The tagging agent solution preferably contains tagging agents including functionalized, antibody-magnetic bead complexes that have antibodies specific to particular cells or other particles. The immuno-modified beads are preferably of magnetic beads of any suitable nature, and may be paramagnetic, diamagnetic, and/or ferromagnetic, or made of any suitable material that can be directed by force vectors in the presence of a magnetic field. Furthermore, the magnetic beads may be of various sizes and/or magnetic strength; for example, during mixing of the tagging agent solution and the sample, beads having a stronger magnetic strength (e.g., larger or made of a strongly magnetic material) may selectively bind to one sample particle type, while beads having a weaker magnetic strength (e.g., smaller or made of weakly magnetic material) may selectively bind to another sample particle type. However, the tagging agent may include any suitable substance chosen for its specific binding capacity for a particle in the sample being analyzed, including antibodies, proteins selected from combinatorial libraries or by some other means, nucleic acids, or any suitable binding substance. These binding substances can be bound to particles by covalent bonding, ionic bonding, and/or other suitable mechanism taking advantage of certain particle properties such as specific size, weight, ionic or electrical charge, and magnetic properties. The step of mixing is preferably performed in a microfluidic tagging conduit, which is further described below, having features that induce chaotic, and preferably turbulent, mixing of the tagging agent solution and the sample, to increase the efficiency and consistency of the tagging of sample particles.

In one embodiment, the sample is introduced into the tagging conduit through tubing at a high flow rate on the order of 50-300 μL/min that further speeds mixing of the sample and tagging agent solution, and the tagging agent solution is introduced into the secondary channel inlet in a similar manner as the sample. The relative flow rates of the sample and tagging agent solution are preferably adjusted to achieve the desired relative concentrations of sample particles and tagging agents. The flow rates are also preferably adjusted relative to the conduit length to ensure that the sample mixes in the microfluidic device for approximately 5 minutes. The time required for the tagging conduit to complete cell tagging is significantly faster than conventional macroscale approaches that require approximately 20-30 minutes to complete particle tagging. However, flow rates can be adjusted so that the mixing time is any suitable amount of time (e.g., for best efficiency and yield for the particular application of interest).

Figure 5:
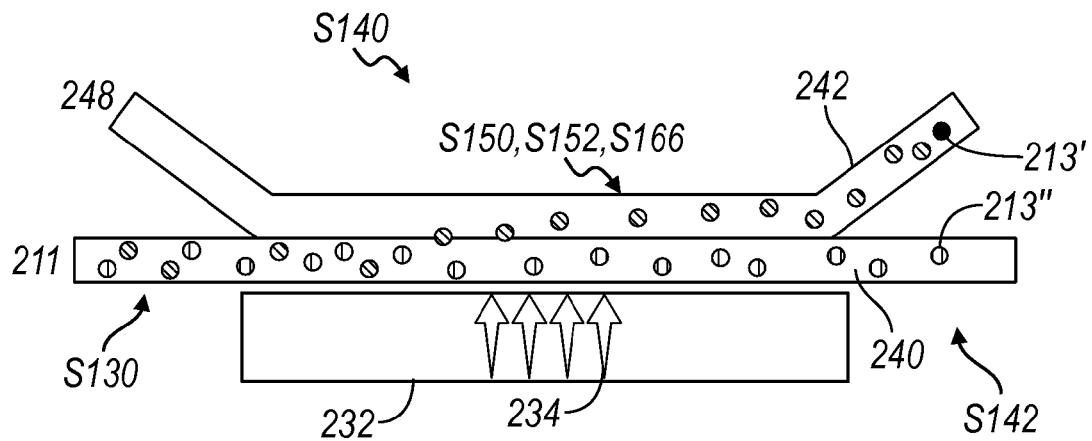
FIGS. 5 and 6 are first and second variations of a diverting embodiment of the magnetic conduit for particle sorting in the system of a preferred embodiment.

The step of passing the sample through a magnetic conduit S130 functions to introduce the sample to a microfluidic magnetic conduit or chamber having a magnetic field that interacts with some or all of the tagged particles. As shown in FIG. 5, the magnetic conduit, further described below, preferably has at least one magnet providing the magnetic field. The sample is preferably passed directly from an outlet of the tagging conduit into an inlet of the magnetic conduit, to provide efficient and continuous flow through the system, but some or all of the sample may alternatively be retained for some time or intermediately utilized for another purpose, such as for another detection, isolation, sample analysis, anti-sedimentation operation, and/or storage step.

Figure 6:
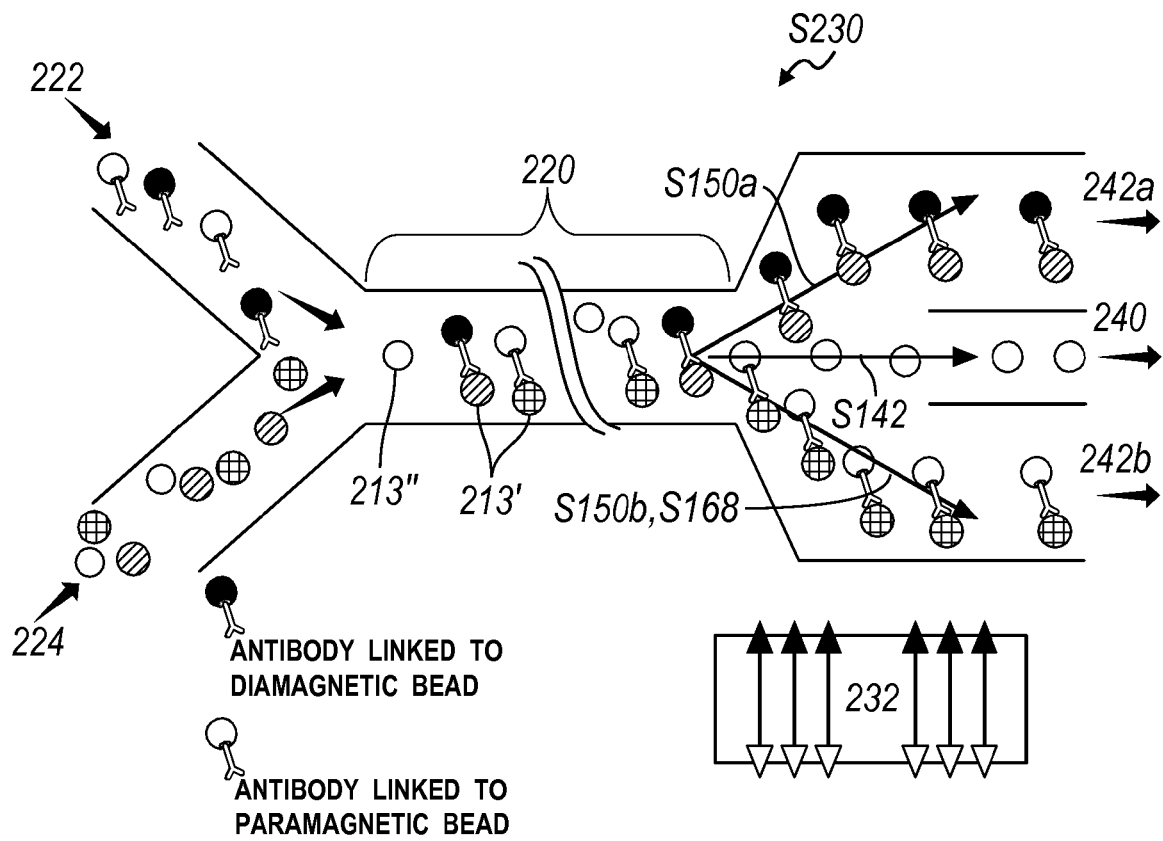

The step of sorting the particles S140 functions to separate the particles into multiple groups according to type, and preferably as a result of the interaction between the tagged particles and the magnetic field of the magnetic conduit. The step of sorting is preferably one or more of several embodiments, and the magnetic conduit structures for facilitating these embodiments are further described below. In a first "diverting" embodiment, as shown in FIGS. 5 and 6, the step of sorting the particles includes: allowing at least some of the untagged particles to flow through a first outlet of the magnetic conduit S142, thereby forming a first group; and diverting at least a first portion S150a of the tagged particles to flow through a second outlet of the magnetic conduit, thereby forming a second group. The step of sorting may further include diverting a second portion S150b of the tagged particles to flow through a third outlet of the magnetic conduit to form a third group, and so on for additional separate groups of particles. Diverting a portion of the tagged particles may include diverting the group of particles into a buffer stream S152 distinguishable from the main sample flow. The sorting step may be one or more of multiple variations in this first embodiment. In a first variation, as shown in FIG. 6, the outlets of the magnetic conduit branch and diverge at substantially the same location along the conduit, such that diverting the first portion of tagged particles and diverting the second portion of tagged particles are performed at substantially the same time. In a second variation, the outlets of the magnetic conduit are positioned serially, such that diverting the first portion of tagged particles and diverting the second portion of tagged particles is performed are performed sequentially; for example, diverting the second portion of tagged particles may be performed downstream of diverting the first portion of tagged particles. In a third variation, aspects of the first and second variations may be combined in any combination and/or permutation; for example, first and second groups of tagged particles may be diverted simultaneously, followed by a third group, further followed by a fourth group. In any of these variations, the magnetic field may be utilized to divert the particles in one or more of several ways. In a first example, the step of sorting includes allowing the magnetic field to repel at least some of the tagged particles S166 (e.g., tagged with diamagnetic beads) towards a particular outlet. In a second example, the step of sorting includes allowing the magnetic field to attract at least some of the tagged particles S168 (e.g., paramagnetic beads) towards a particular outlet. In a third example, as shown in FIG. 6, the magnetic field repels and/or attracts at least some of the tagged particles such that particular force vectors selectively direct the tagged particles into particular outlets. Furthermore, the magnetic field may repel and/or attract the tagged particles to different degrees. As a fourth example with five dimensions of particle sorting, five different particle types may be tagged with magnetic beads of various sizes, magnetic strength ("magnetic charge") and/or kinds that interact differently with the magnetic field. In this example, in a magnetic conduit having a magnet at its bottom surface and five outlets positioned at increasing distance from the bottom surface, a particle tagged with a large diamagnetic bead is repelled by a large degree into a first, uppermost outlet, a particle tagged with a small diamagnetic bead is repelled by a small degree into a second outlet, an untagged particle may be unaffected by the magnetic field and pass undeflected into a third outlet, a particle tagged with a small paramagnetic bead is attracted to a small degree to a fourth outlet, and a particle tagged with a large paramagnetic bead is attracted to a large degree to a fifth, lowermost outlet. Other versions of this first embodiment of the sorting step include every combination and permutation of these variations of the sorting step and magnetic field interactions.

Figure 7:
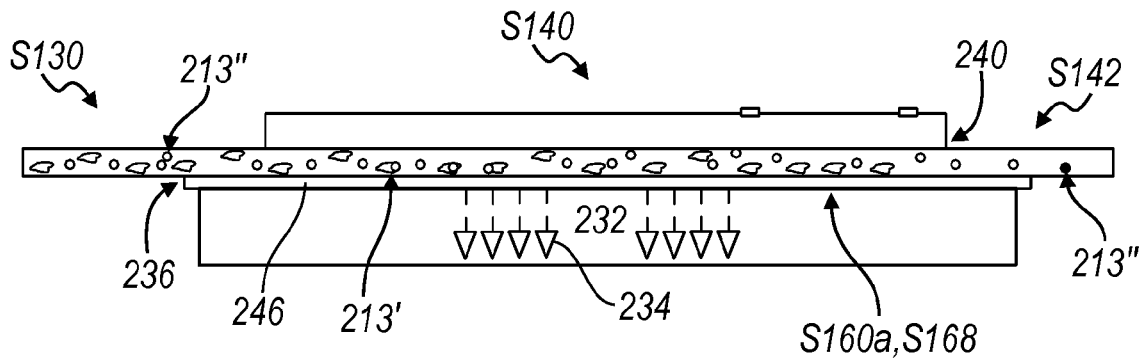
FIGS. 7-11 are variations of a capture embodiment of the magnetic conduit for particle sorting in the system of a preferred embodiment.
Figure 8:
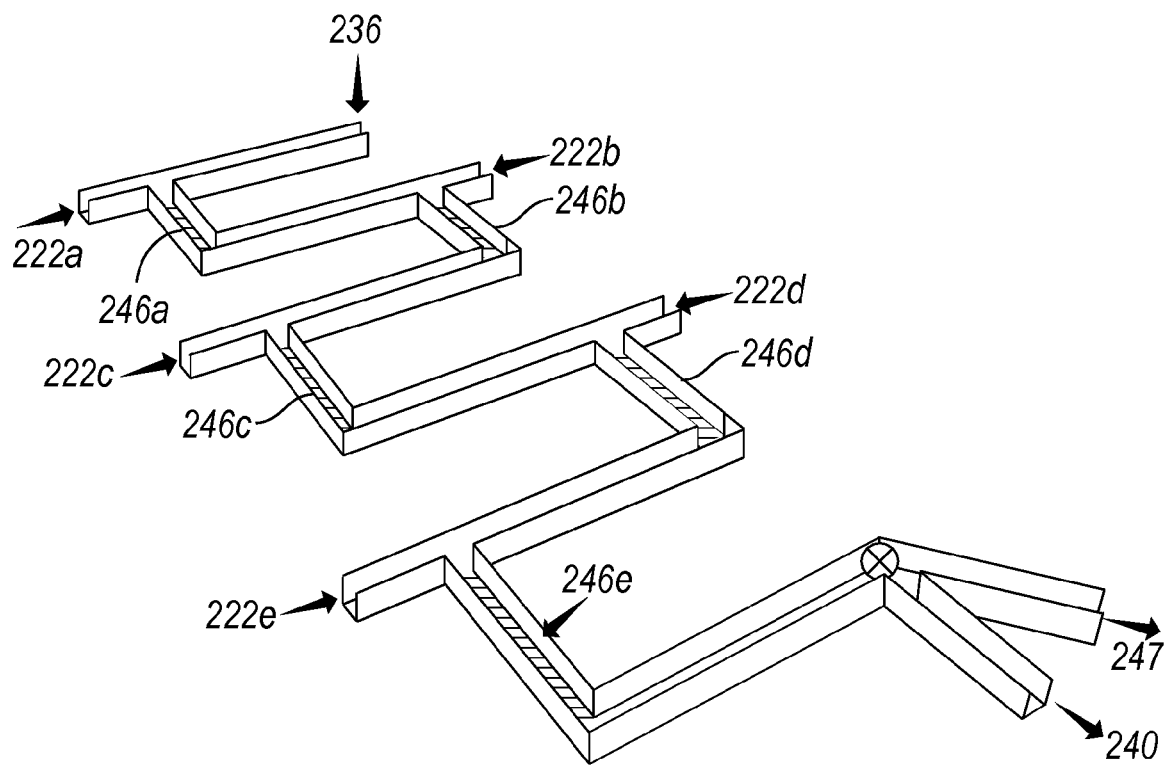
Figure 9A:
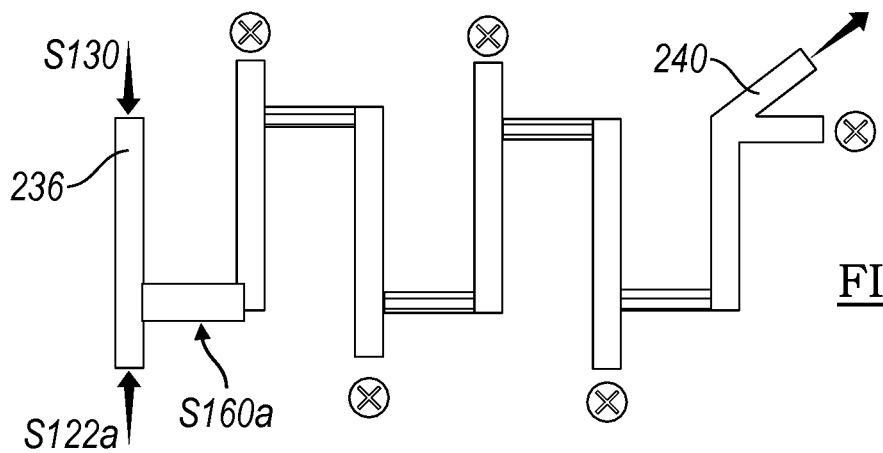
Figure 9B:
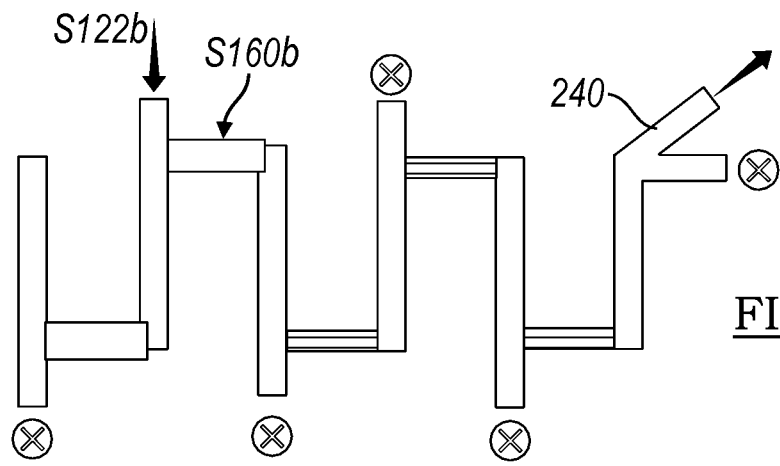
Figure 9C:
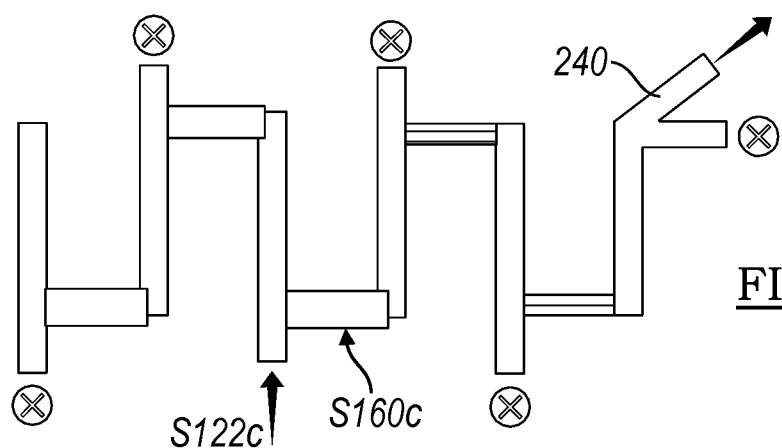

In a second "capture" embodiment, as shown in FIGS. 7-9, the step of sorting S140 includes: allowing at least some of the untagged particles to flow through a first outlet of the magnetic conduit S142, thereby forming a first group; and capturing at least a first portion of the tagged particles S160a on a first surface of the magnetic conduit, thereby forming a second group. The step of sorting may further include capturing a second portion of the tagged particles S160b on a second surface of the magnetic conduit to form a third group, and so on for additional separate groups of particles (S160c, etc.). The sorting step may be one or more of multiple variations in this second embodiment. In a first variation, the first surface for capturing a first portion of tagged particles is substantially at the same location as the second surface for capturing a second portion of tagged particles; for example, the magnetic field may attract the first portion towards the first surface while simultaneously repelling the second portion towards the second surface.

Figure 10:
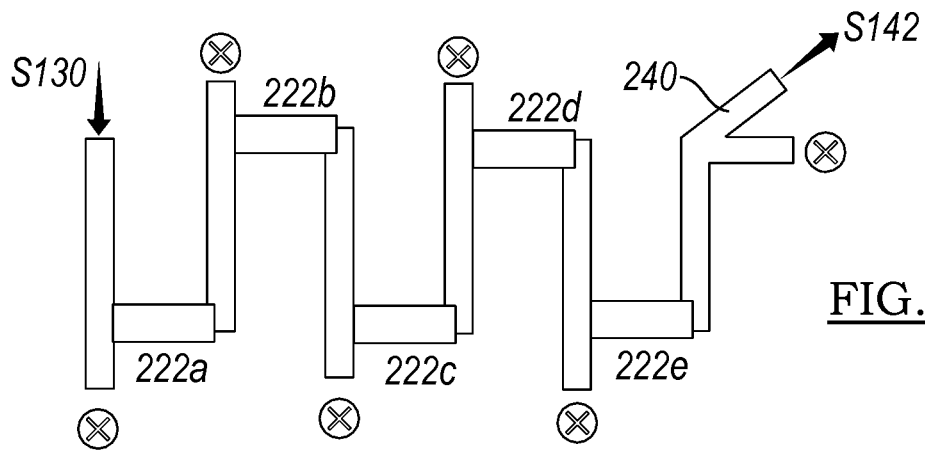

In a second variation, as shown in FIG. 9, the first and second capture surfaces are located sequentially along the magnetic conduit; for example, capturing the second portion of tagged particles S160b on a second surface may be performed downstream of capturing the first portion of tagged particles on a first surface S160a. In this second variation, the method may further include mixing with the sample a second stream of tagging agent solution S122b for selectively binding to particles, and may further include mixing third (S122c) and fourth streams, and so on. At least a portion of the successive streams of tagging agent solution are preferably introduced and mixed with the sample downstream of the first stream, such that each group of particles is tagged and captured at each of multiple stages along the magnetic conduit. Alternatively, as shown in FIG. 10, the multiple streams of tagging agents may first be captured on separate surfaces prior to passing the sample through the magnetic conduit, such that in one pass of the sample through the magnetic conduit, sample particles selectively bind to separated captured tagging agents and are sorted onto the various surfaces.

In a third variation, the step of sorting may include any combination and/or permutation of the first and second variations, capturing some groups of tagged particles at substantially the same location, while capturing other groups of tagged particles at sequential locations along the magnetic conduit. Similar to the first embodiment, in any of these variations, the magnetic field may be utilized to capture the particles in one or more several ways (repelling and/or attracting tagged particles to a particular surface).

Figure 11A:
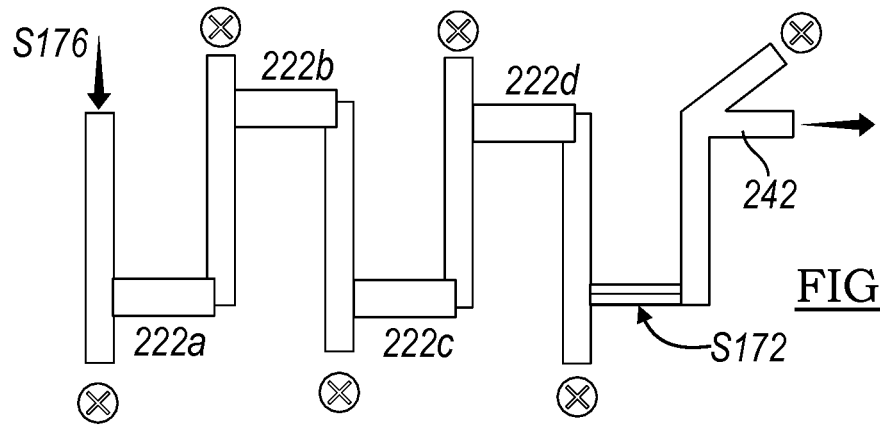
Figure 11B:
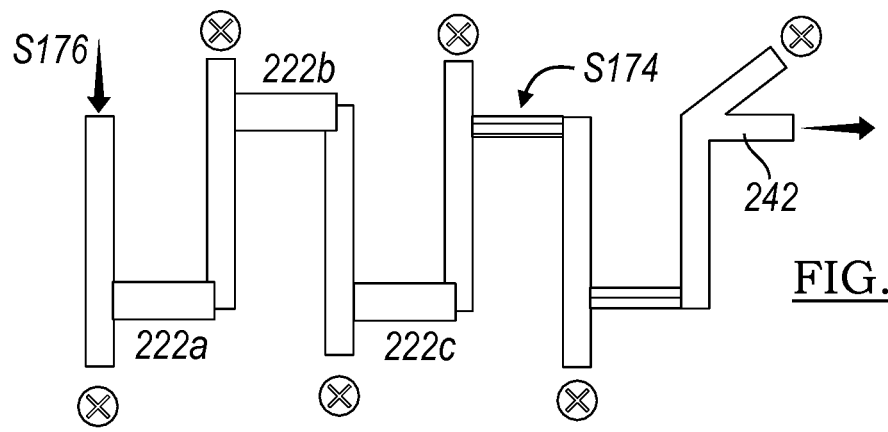

In the second embodiment, as shown in FIG. 11, the step of sorting preferably further includes removing the magnetic field S170 to release the captured particle groups, which may include deactivating an electromagnet providing the magnetic field, and/or introducing a magnetic shield or other substance to divert magnetic force vectors to release the captured particle groups. Removing the magnetic field may be performed in multiple steps, such as if different groups of particles are captured in different regions, such that removing includes removing a first portion of the magnetic field S172 and removing a second portion of the magnetic field S174. For example, in embodiments of the method in which different groups of particles are captured in sequential downstream order on serial magnetic capture surfaces of a magnetic conduit, the magnetic fields of the surfaces may be removed sequentially in reverse order of capture to allow the sorted particles to exit separately. The step of sorting may alternatively and/or additionally include introducing a stream of buffer S176 or other fluid at a velocity strong enough to cause the captured particle groups to "break free" from the magnetic force.

Figure 16:
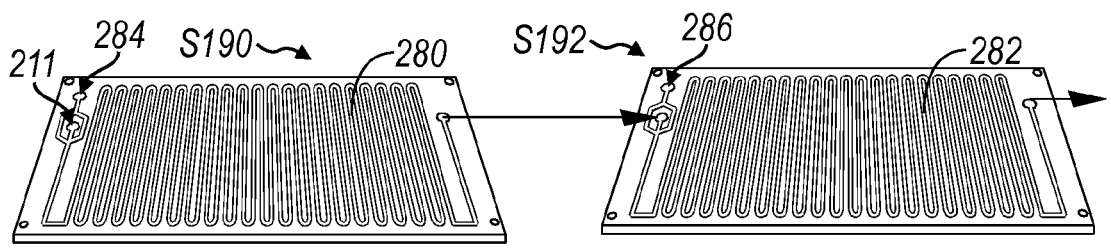
FIG. 16 is a schematic of the fixation and permeabilization module of the system of a preferred embodiment.

In some embodiments of the method, as shown in FIG. 16, the method further includes fixing the cell membranes S190 of at least some of the cells in the sample with a fixation solution that rigidifies membranes of cells in the sample, and permeabilizing at least some of the fixed cell membranes S192 with a permeabilization solution, and may further include washing the sample with a diluting solution to eliminate adverse effects of permeabilization agents. An example of a fixation solution that may be used to fix cell membranes is formaldehyde, and an example of a permeabilization solution is methanol. However, the fixation and permeabilization solutions chosen can include any suitable solution to rigidify and permeabilize cell membranes. In these embodiments, the step of mixing with a tagging agent solution preferably includes allowing tagging agents to bind to at least one type of intracellular particle, such as proteins, organelles, nucleic acids, and/or other substances of interest. In these embodiments, the tagging agents are preferably sized to pass through openings in the cell membranes. In this manner, the method may allow tagging agents to selectively bind to either one of or both external cell or other particle receptors (i.e. extracellular portions of membrane-bound particles) and internal (i.e. intracellular) particles of interest, such that the step of sorting the sample particles may additionally and/or alternatively be based on extracellular and/or intracellular characteristics of the sample particles.

In some embodiments of the method, as shown in FIG. 12A-D, the method further includes the step of lysing at least some of the untargeted sample particles S180 with a lytic solution that selectively lyses particles of at least one of the sample particle types. The step of lysing functions to selectively deplete untargeted particles, or particles not of interest. The step of lysing is preferably performed prior to the step of tagging particles and/or the step of passing the sample through a magnetic conduit, to reduce or eliminate common or plentiful untargeted particles prior to these steps, thereby increasing the relative presence of ordinarily rarer target cells and improving efficiency of particle sorting. As one example, the step of lysing may be performed before the step of tagging particles, such that the step of tagging particles includes tagging intracellular particles like proteins and nucleic acids that are released from lysed cells. However, the step of lysing may alternatively and/or additionally be performed after these or any suitable step. The step of mixing the sample with a lytic solution S180 preferably destroys certain untargeted sample particles such as cells by exploiting the differences in osmotic resistances of different particles, causing selective lysis during exposure of the sample to hypotonic and/or hypertonic solutions of lytic agents in a controlled manner. One example of a lytic solution is deionized water to lyse erythrocytes in a blood sample, although any suitable lytic agent may be used. The step of mixing the sample with a lytic solution is preferably performed in a microfluidic lysing conduit, further described below, having features that induce chaotic, and preferably turbulent, mixing of the lytic solution and the sample. In these embodiments, the method preferably further includes neutralizing the sample with a buffer solution, which returns the sample to isotonic conditions after exposing the sample to the lytic solution.

Figure 15:
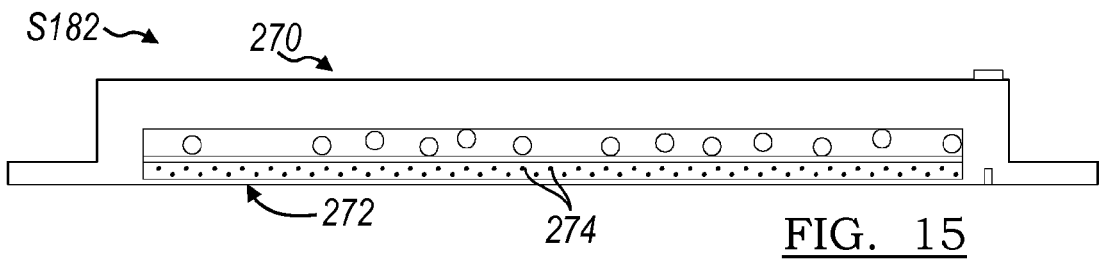
FIG. 15 is a schematic of the immunoaffinity chamber of the system of a preferred embodiment.

In some embodiments of the method, as shown in FIG. 15, the method further includes the step of capturing particles of at least one of the sample particle types based on immunoaffinity S182. The step of capturing particles S182 functions to isolate particles of at least one of the sample particle types, for analysis of the captured particles and/or to deplete the captured particles (such as if they are untargeted cells or proteins) from the sample. Similar to the step of lysing, the step of capturing particles S182 based on immunoaffinity is preferably performed prior to the step of tagging particles and/or the step of passing the sample through a magnetic conduit to improve the efficiency of particle sorting. However, the step of capturing particles may additionally and/or alternatively be performed after these or any suitable step. As one example, the step of capturing particles based on immunoaffinity may be performed after the step of lysing, to capture intracellular particles that are released from lysed cells. The step of capturing particles based on immunoaffinity preferably includes passing the sample through a chamber or conduit, further described below, having a surface with capture particles that selectively bind to and capture at least one of the sample particle types based on immunoaffinity between the capture particles and the sample particle types. In one embodiment, the capture particles may be antibodies or antibody mimetics functioning as capture particles lining the surface of the chamber, and these capture particles are specific to certain sample particle types such that the antibodies selectively bind to and immobilize the certain sample particle types. The capture particles may be specific to targeted particles of interest and/or untargeted particles not of interest, depending on the particular application of the method.

In some embodiments of the method, the method further includes the step of filtering the sample particles in the sample based on size. The step of filtering may be performed with a mesh screen, semi-permeable membrane or filter, such as one made of a micromesh material that permits sample particles only below a certain size to pass through. The method may additionally and/or alternatively include the step of filtering based on relative density or specific gravity, permeability, ionic charge, or another suitable physical property. Similar to the steps of lysing and capturing particles based on immunaffinity, the step of filtering particles in this way is preferably performed prior to the step of tagging particles and/or the step of passing the sample through a magnetic conduit to improve the efficiency of particle sorting, but may additionally and/or alternatively be performed after these or any suitable step.

In some embodiments of the method, the method further includes the step of removing unbound tagging agents S310 that are not bound to sample particles during the step of tagging S120. The step of removing unbound tagging agents S310 is preferably performed after the step of tagging S120 and may be performed before and/or after the step of sorting the sample particles S140. As shown in FIG. 17, removing unbound tagging agents S310 from a sample stream preferably includes mixing the sample with a solution of tagging sponges S312 that bind to the unbound tagging agents in the sample stream, and sorting the tagging sponges S314 based on the interaction between the tagging sponges and a second magnetic field in a second magnetic conduit. The tagging sponges are preferably similar to tagging agents, except that the tagging sponges are specific to the functionalized end of the unbound tagging agents. For example, in an embodiment in which the tagging agent is a magnetic bead functionalized with an antibody, the tagging sponge is preferably a magnetic bead functionalized with an antigen specific to the antibody of the tagging agent. Alternatively, depending on the binding characteristic of the tagging agent, the tagging sponge may be functionalized with a protein, immunoglobulin, nucleic acid, and/or any suitable binding substance. Like the tagging agents, the tagging sponge may include a diamagnetic, paramagnetic and/or ferromagnetic bead of any suitable size and shape. The step of mixing S312 is preferably performed in a structure similar to that for the step of tagging S120, and the step of sorting the tagging sponges S314 is preferably similar to the step of sorting sample particles S140. For example, in an embodiment in which the tagging agent is a small diamagnetic bead repelled by the magnetic field and the tagging sponge is a large paramagnetic bead attracted to the magnetic field, the bound tagging agent-tagging sponge complexes would have a net attraction to the magnetic field. The net attraction thereby allows the capture or deflection to another outlet the tagging agents not bound to sample particles (similar to the "capture" and "diverting" embodiments of the sorting step S140) while allowing tagging agent-sample particle complexes to flow through the second magnetic conduit.

Figure 18A:
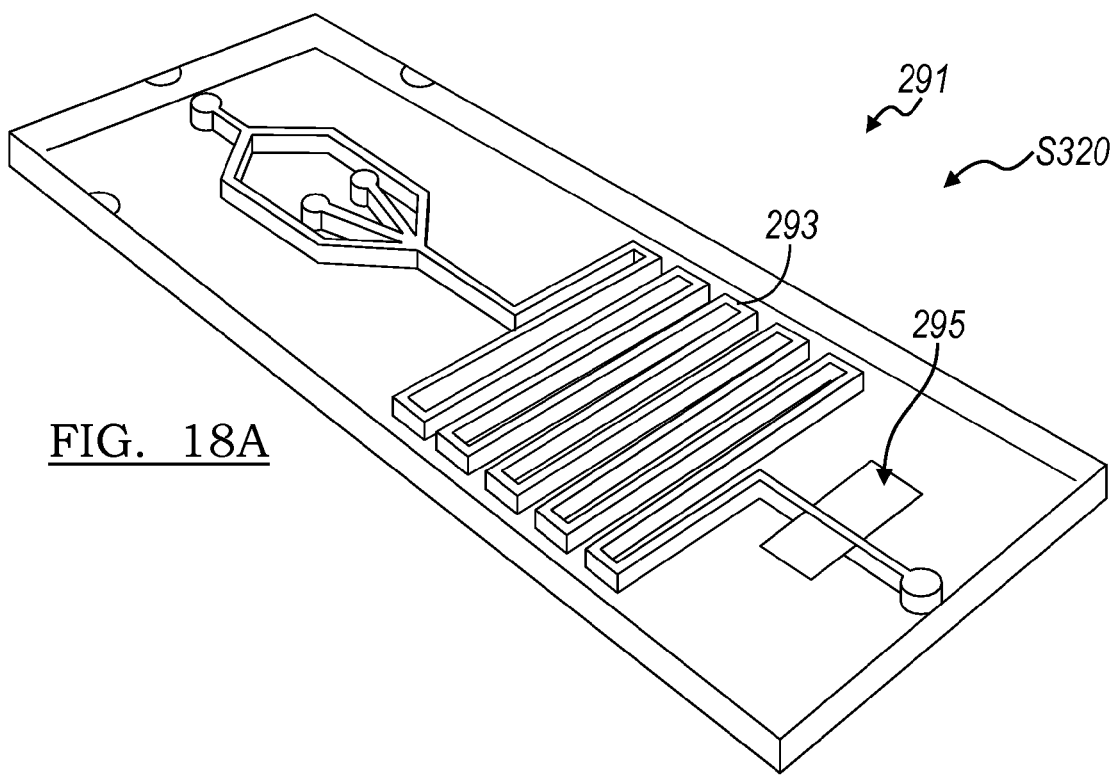
FIGS. 18A and 18B are overall and detailed schematic views, respectively, of the particle detection apparatus of the system of a preferred embodiment.
Figure 18B:
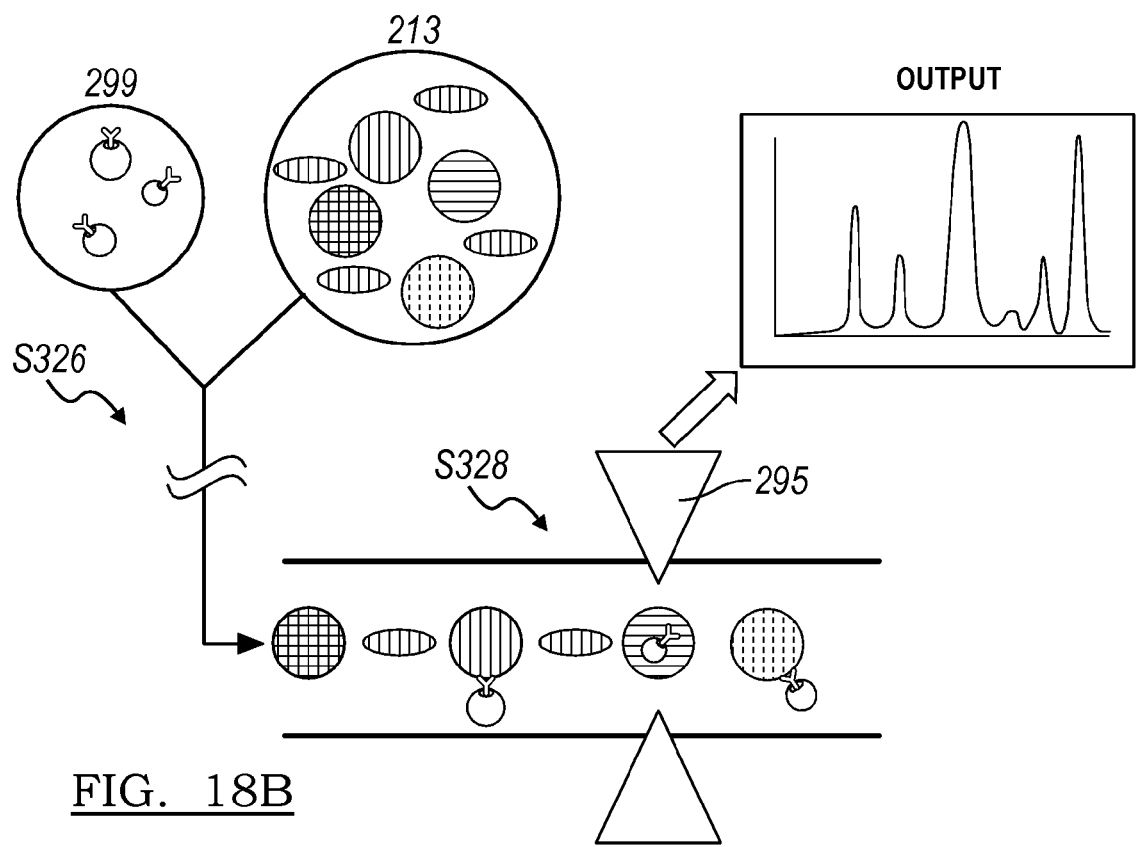

In some embodiments of the method, the method further includes the step of enumerating particles S320 in one or more of the separated groups. Enumerating particles S320 in the separated groups functions to quantify the number of particles in at least one group of a particular sample particle type, thereby obtaining an estimate of the occurrence of the sample particle type in the sample, such as for diagnostic, therapeutic, or other analytical applications. Enumerating particles preferably includes obtaining an initial measurement of an electrical characteristic S322 across two electrodes (FIG. 19B), obtaining a secondary measurement S324 of the electrical characteristic across the electrodes with a group of particles between the electrodes (FIG. 19C), computing the difference between the initial and secondary measurements, and generating an estimate of the number of captured particles based on the computed difference. The electrical characteristic may be impedance, resistance, capacitance, or any suitable characteristic. Obtaining the initial and secondary measurements may be performed at a location where particles of a particular group are captured such as within the magnetic conduit, before and after particle capture, but these measurements may be obtained in any suitable location, such as in individual chambers that hold grouped particles after filtering, after capture and/or capture and release of particles grouped by immunoaffinity, or after being diverted into groups by the magnetic conduit. Generating an estimate of the number of captured particles based on the computed difference preferably includes performing a ratio calculation using the computed different and a known or expected value of the electrical characteristic for a unit number of particles of that particle type (such as for 5, 10, or 25 particles). These steps may be used to enumerate whole particles such as cells, extracellular, and/or intracellular particles such as proteins, nucleic acids, organelles, and metabolites directly or indirectly via binding to additional beads and/or particles. In another embodiment, the step of enumerating particles includes capturing a group of particles on a fixed post, similar to capturing based on immunoaffinity S182, and quantifying the binding events on the posts. As is known to one skilled in the art, enumerating the binding events on the posts may be similar to detecting and counting binding events in protein microarrays, or any suitable method of enumerating binding events. The step of enumerating particles may additionally and/or alternatively include other suitable methods of enumeration, including electrochemical detection, surface-enhanced Raman scattering (SERS), thermal detection, fluorescence detection methods such as those used in flow cytometry and/or other impedance-based detection methods that are well known in the art. Generally speaking, as shown in FIG. 18B, the preferred and alternative methods of enumeration may include labeling tagged sample particles with a labeling reagent S326 (such as an electrochemical tag, fluorescent tag, a nanoparticle, or other suitable labeling reagent, selected for its applicability in the detection method) and detecting the labeled particles S328.

In some embodiments of the method, the method further includes the step of recirculating at least a portion of the sample S330 to the body of the patient or other original source of the biological fluid sample, such as through a catheter setup similar to dialysis machines, particularly embodiments in which the sample is blood or cerebrospinal fluid. In one variation, the step of recirculating includes modifying the sample and returning at least a portion of the sample to the body of the patient. The step of modifying may include: removing selected particles or substances from the sample, such as one or more of the groups separated by the sorting step of the method; adding selected particles or substances to the sample, such as one or more of the groups separated by the sorting step of the method; and/or adding a therapeutic agent S332, such as a therapeutic drug or nutrients from one or more reservoirs. As an example, the therapeutic agent may be administered based on the results of enumerating groups of particles or other analysis of the separated groups of particles (e.g. percentage of cells with intracellular particles of interest), additional treatment recommendations, and/or any suitable basis for therapy.

2. Microfluidic System for Isolating Particles

As shown in FIG. 1, the microfluidic system 200 for isolating particles of a preferred embodiment includes a sampling module 210 including a cannula coupled to the patient that obtains a sample of biological fluid directly from the patient, wherein the sample contains particles of multiple sample particle types; a microfluidic tagging conduit 220, fluidly coupled to the sampling module 210, having a first inlet that receives the sample, a second inlet that receives a solution of magnetic tagging agents that selectively bind to and tag particles of at least one particle type, and a textured surface that induces mixing of the particles and tagging agents; and a microfluidic magnetic conduit, fluidly coupled to the tagging conduit and having at least one magnet providing a magnetic field that interacts with at least a portion of the tagged particles, in which the magnetic field sorts the particles in the sample into at least two groups based on the interaction between the tagged particles and the magnetic field.

The sampling module 210 functions to receive a sample of biological fluid from the patient for analytical purposes. As shown in FIG. 2, the sampling module preferably includes a cannula 212, and more preferably a catheter coupled to the patient that obtains the sample. As one example, the catheter may obtain a blood sample from the patient through an arterial line, an intravenous line, a peripherally inserted central catheter (PICC), a central line, and/or an in-dwelling catheter. As another example, the catheter may obtain cerebrospinal fluid sample through an external ventricular drain (EVD) or a lumbar drain. As another example, a Foley catheter or a suprapubic catheter may be used to obtain a urine sample. However, the cannula may alternatively be any suitable kind of device for obtaining a sample of biological fluid. The sampling module preferably at least partially mounts on or near the patient, to enable the system to perform particle isolation more immediately after the sample is taken from the patient, such as for diagnostic or other analytical purposes. For example, the system may be appropriate in cases such as when the sample is a fluid that degenerates or otherwise changes relatively quickly and must be analyzed soon after being obtained to achieve accurate results; when the sample is difficult to safely store before particle isolation and/or analysis can be performed; or any other suitable situation that requires swift and immediate particle isolation and/or analysis. The sample may be blood, cerebrospinal fluid, urine, and/or any suitable biological fluid and preferably contains particles of multiple sample particle types. For example, a blood sample typically includes more common particle types like erythrocytes and leukocytes, rare particle types like proteins and nucleic acids, and may or may not include rare potential particle types of interest like circulating tumor cells.

Figure 3A:
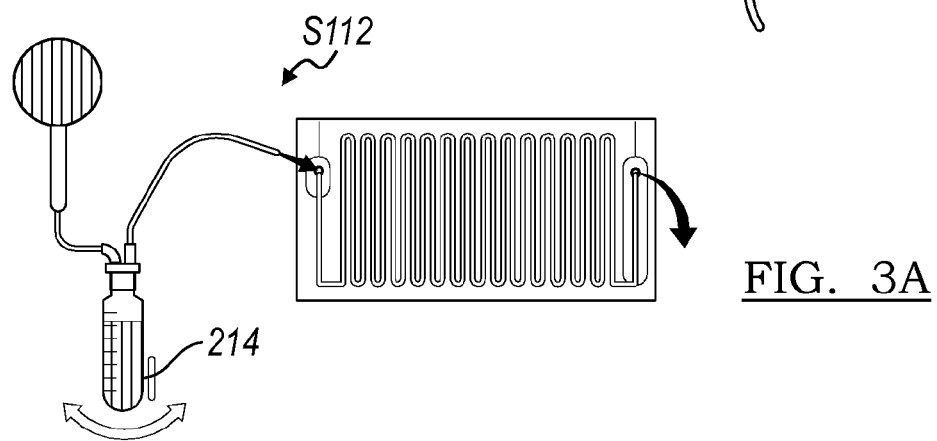
FIGS. 3A and 3B are schematics of rocker and rotating mechanisms, respectively, for reducing particle sedimentation of a sample.
Figure 3B:
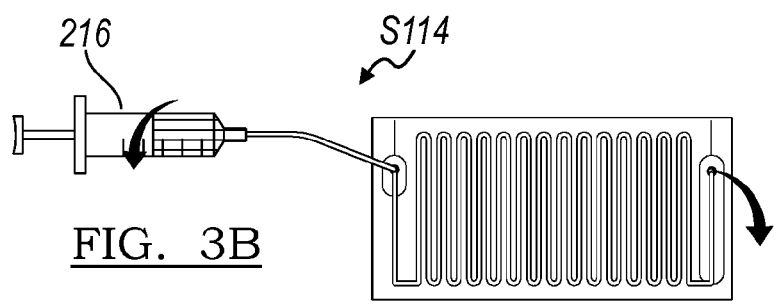

As shown in FIG. 3 the sampling module may further function to prepare the sample by maintaining a uniform distribution of particles throughout the sample. For example, cell sedimentation, which typically occurs at rates on the order of 1 μm/sec, is undesirable because sedimentation leads to a non-uniform distribution of cells in the sample, and the devices of the system ideally handle samples with uniform cell distribution such that a sample input of a certain volume contains a fixed and known number of cells. The sampling module preferably includes a perturbing mechanism that prepares the sample by moving in a manner that reduces sedimentation of the particles in the sample, and a sample transfer device that drives the sample into the perturbing mechanism. The perturbing mechanism of the sample delivery module may be a rocker (FIG. 3A) that continuously and gently rocks back and forth to agitate the sample and prevent sedimentation. Alternatively, the perturbing mechanism may be a rotating mechanism (FIG. 3B) such as a horizontally oriented syringe pump that continuously rotates like a cement truck to prevent sedimentation. The perturbing mechanism may, however, be any suitable mechanism that prevents or reduces sedimentation in any suitable manner.

The sample transfer device of the sampling module functions to drive the sample into the perturbing mechanism. The sample transfer device is preferably a tubing or a channel through which fluid may flow driven by a pressure source such as a dialysis roller pump, syringe pump or balloon, or vacuum tubing, but may alternatively be any suitable device or method that aids delivery of the sample from the cannula to the perturbing mechanism. In some embodiments, the sampling module additionally and/or alternatively functions to transport and prepare tagging agents such as immuno-modified beads in a solution, to maintain a solution of uniformly distributed tagging agents. The perturbing mechanism that prepares the tagging agents is preferably similar to the perturbing mechanism of the preferred embodiment that prepares the sample.

The microfluidic tagging conduit 220 functions to distinguish multiple sample particle types from each other, for example, to distinguish targeted particles of interest from untargeted particles not of interest. This is preferably accomplished with the use of tagging agents 223 in a rapid, highly efficient manner, to reduce processing time and increase consistency of tagging. Tagging agents preferably selectively bind to certain particles. The tagging agents may bind to and label particles of interest in the sample, or bind to and label undesired particles in the sample. As shown in FIG. 5, the tagging agents are preferably magnetic beads that are functionalized with antibodies that are specific to at least one selected particle type, such that the antibodies bind the magnetic beads to certain particles, creating tagged particles 213' and untagged particles 213" in the sample. The mechanism for binding may additionally and/or alternatively be any substance chosen for its specific binding capacity for a particle in the sample, including antibodies, proteins selected from combinatorial libraries or by some other means, nucleic acids, or any suitable substance, which can be linked to a particle through covalent bonding, ionic bonding, or some other mechanism including but not limited to specific size, weight, ionic/electrical charge, and magnetic properties that can be exploited for tagging particles. The tagging agents 223 may be paramagnetic (attracted to a magnetic field source and retaining magnetic properties as long as the magnetic field is present; such as magnesium, molybdenum, lithium, and tantalum), diamagnetic (repelled by a magnetic field source and retaining magnetic properties as long as the magnetic field is present; such as copper, silver, and gold), and/or ferromagnetic (attracted to a magnetic field source and permanently retaining magnetic properties following exposure to a magnetic field even after the field is no longer present; such as iron, nickel, and cobalt). However, the magnetic beads may alternatively be any combination of any suitable kinds of beads appropriate for the specific application. Furthermore, the magnetic beads may be of various sizes and/or magnetic strength; for example, during mixing of the tagging agent solution and the sample, beads having a stronger magnetic strength (e.g., larger or made of a strongly magnetic material) may selectively bind to one sample particle type, while beads having a weaker magnetic strength (e.g., smaller or made of weakly magnetic material) may selectively bind to another sample particle type. The tagging conduit preferably achieves a pre-determined ratio of particles to tagging agents that is uniform throughout the entire sample.

As shown in FIG. 4, to tag sample particles, the microfluidic tagging conduit 220 preferably places particles of the sample 211 in proximity to tagging agents 223 through a combination of rapid diffusion and rapid mixing to initiate binding events of the tagging agents binding to particles. The tagging conduit preferably includes a confined microscale channel in which the sample and tagging agent solution 221 mix chaotically, and preferably turbulently, to enhance the process of the tagging agents binding to particles of the sample. As shown in FIG. 4, the conduit geometry is preferably a long serpentine shape. In a preferred embodiment, the tagging conduit includes a main inlet 224 through which the sample 211 enters the tagging conduit, at least one secondary inlet 222 through which the tagging agent solution 221 enters the tagging conduit, and an outlet through which the mixed sample and tagging agent solution exit the tagging conduit. The secondary inlet 222 may divide and flank the main inlet slightly downstream of the secondary inlet.

As shown in FIG. 4, the tagging conduit preferably includes a textured surface 226 that induces mixing of the tagging agent solution and sample. The textured surface preferably includes sets of ridges 228 in a double herringbone pattern, such that the herringbone ridges are aligned in the direction of flow and are arranged in laterally offset rows. This herringbone pattern preferably is laid pointing upstream, such that the fluid flow induces rotational mixing along the central axis of the conduit from the outside of the conduit towards the inside of the conduit, but may be laid in any suitable orientation, preferably one that optimizes turbulent mixing. Both the serpentine path and herringbone ridge pattern of the conduit contribute to higher speed and higher efficiency of binding events than conventional tagging methods by encouraging sample and tagging agent solution mixing. Alternatively, the conduit may have any suitable pattern of ridges, transverse posts, recesses, and/or any suitable physical features to encourage mixing between the sample and tagging agent solution.

In one specific example, the conduit preferably has a cross-section of approximately 100 μm×100 μm and ridges with a height of 25 μm, but may alternatively have any suitable microscale dimensions such that the channel ensures rapid diffusion for increased rate of binding events between cells in the sample and tagging agents. Alternatively, the particle tagging microfluidic device may include channels of any suitable size, geometry, and number. The tagging conduit is preferably a microfluidic device manufactured with soft lithography techniques. Soft lithography processes are known and used in the art of manufacturing microscale devices, and the implementation of soft lithography processes in the microfluidic device would be readily understood by a person of ordinary skill in the art. The microfluidic device is preferably a silicon wafer treated with oxygen plasma in an asher and spin coated with a negative photoresist such as SU-8. To create the tagging conduit, a transparency mask with a negative of the channel pattern is used in photolithography, and the elastomer polydimethylsiloxane (PDMS) or another suitable stamp resin is mixed with a cross-linker in a ratio of approximately 10 parts stamp resin to 1 parts cross-linker and poured onto the treated silicon wafer. After the silicon wafer cures at a preferable temperature of 60° C. for a preferable curing time of 12 hours, the PDMS is released. Conduit inlets, conduit outlets, and any additional desired conduit access holes are preferably created by puncturing the channel walls with a 22 gauge needle, but the channel access holes may alternatively be created with any suitable size needle or other device. Tubing of a diameter slightly larger than the diameter of the conduit access holes is preferably pressed into the conduit inlets and outlet to provide the sample and the tagging agent solution access in and out of the tagging conduit.

The microfluidic magnetic conduit 230, which preferably includes at least one magnet 232 providing a magnetic field 234 that interacts with some or all of the tagged particles, functions to sort particles in the sample into two or more groups according to sample particle type, based on the interaction between the tagged particles and a magnetic field. The magnet 232 in the magnetic conduit is preferably an electromagnet, but may be an electromagnetic coil, a permanent magnet, magnetized metal contacts, and/or any other suitable source of a magnetic field. The magnet is preferably removable, coverable, and/or retractable. As an example, an electromagnetic coil may be configured to produce a magnetic field and capture tagged particles, and then may be reconfigured to remove the magnetic field and release tagged particles. As another example, magnetized metal contacts along the floor of the magnetic conduit may be uncovered to produce a magnetic field and capture tagged particles, and then may be covered to remove the magnetic field and release the captured particles. The magnet is preferably located along at least a portion of the bottom external surface of the conduit, but may alternatively be located on the side, the top, and/or another external surface, on the internal surface of the conduit, or within the conduit material on any suitable side of the conduit. The conduit 230 may include multiple magnets that create a suitable magnetic field within the conduit.

The magnetic field may interact with the tagged particles in any suitable manner to selectively capture portions of the tagged particles. As described above, the magnetic field may utilize magnetic attraction and/or repulsion in various manners to direct tagged particles towards particular surfaces, thereby sorting particles of the sample according to their magnetic nature. For example, the magnetic field may attract paramagnetically- and/or ferromagnetically-tagged particles, or repel diamagnetically-tagged particles. In this manner, the magnetic forces may affect different tagged particles in different ways, such as in direction and/or magnitude of force. The magnetic field generated by the magnet is preferably strong enough to generate a magnetic force appreciably larger than the hydrodynamic drag force acting on the tagged cells to quickly attract and/or repel the tagged particles without impeding flow and without damaging iron-containing cells such as erythrocytes. The appropriate magnetic field strength for the specific application of the system depends on multiple other factors, such as sample flow rate, sample viscosity, and sample particle composition.

Generally, the magnetic conduit may be straight, similar to a rectangular chamber, but may be serpentine, such as to increase available conduit length while reducing footprint. The structure of the magnetic conduit is preferably at least one of a couple of embodiments. In a first embodiment ("capturing"), the magnetic conduit includes an outlet 240 through which untagged particles flow to form a first group and at least one surface for capturing and immobilizing at least a portion of tagged particles to form a second group. As shown in FIG. 7, as the sample flows through the magnetic conduit through inlet 236, the particles 213' tagged with a magnetic tagging agent or have an inherent magnetic property are preferably directed towards and immobilized on the surface 246, and untagged or nonmagnetic particles 213" are preferably allowed to flow through the outlet 240. After untagged particles 213" pass through the outlet, the magnetic field is preferably removed to release the captured cells, although additionally and/or alternatively a buffer may be passed through the chamber and/or another suitable release process may be utilized. In the "capture" embodiment, the magnetic conduit may further include a second surface 246b for capturing and immobilizing a second portion, distinct from the first portion, of tagged particles to form a third group, and third, fourth, or more surfaces for capturing and immobilizing additional portions of tagged particles to form multiple groups. The multiple capturing surfaces may be located at substantially the same location along the magnetic conduit. However, as shown in FIG. 8, some or all of the capturing surfaces may be located at different stages along the conduit. For example, a second surface 246b at one stage for capturing tagged particles may be located downstream of a first surface 246a at another stage for capturing tagged particles, separating captured particles at distinct stages along the conduit.

In the "capturing" embodiment, the magnetic conduit may include more than one inlet for introducing additional streams of tagging agent solution into the magnetic conduit. For instance, as shown in FIGS. 8 and 9, a multi-stage conduit may include a tagging agent inlet 222 at each stage prior to a capture surface, and each inlet may be controlled by a valve such that as the sample flows through the conduit, the valves may be opened in sequence. In the example shown in FIG. 8, a first tagging agent solution is released through a first tagging inlet 222a. After sufficient binding interaction to tag certain sample particles, the sample continues flowing through a first capture region having a magnetic field that captures the tagged particles on a first capture surface 246a, whereas the remaining untagged particles continue to pass through. A second tagging agent solution is then released through a second tagging inlet 222b located downstream of the first tagging inlet, and after sufficient binding interaction to tag more sample particles, the sample continues flowing through a second capture region having a magnetic field that captures the tagged particles on a second capture surface 246b. The process may be repeated in series as desired for a particular application, until near the end of the magnetic conduit, which may have one or more valved outlets for the remaining part of the sample and/or unbound tagging agents. Alternatively, as shown in FIG. 10, prior to introducing the sample into the magnetic conduit, magnetic tagging agents may be introduced through any suitable number of tagging inlets 222 and captured by an activated magnetic capture region downstream of each tagging inlet. When the sample is introduced into the magnetic conduit, sample particles selectively bind to the captured tagging agents, thereby being sorted into groups. Alternatively, the magnetic conduit may include multiple tagging inlets at the beginning of the conduit such that tagging agents simultaneously selectively bind to their respective specific particles in parallel, and the tagged particles are selectively captured in multiple, serial capture regions of the magnetic conduit. In these versions, following the serial capture of tagged particles, the captured particles may be sequentially released by removing the magnetic field at each capture region (e.g., deactivating an electromagnet at each stage) or any suitable release mechanism and flow through an outlet or any suitable outlet. The captured particles may be released in order of capture, reverse order of capture (FIGS. 11A and 11B), or any suitable order.

In one specific example of the "capturing" embodiment, the magnetic conduit has dimensions on the order of 50 μm height×7 cm length×3 cm width, or any suitable shape and size with an extremely low aspect ratio, including an extremely small dimension along the capture direction, where the capture direction is the direction that tagged cells follow when attracted to or repelled by the magnet. The magnetic conduit, with its low aspect ratio, results in a more efficient and faster cell capture than conventional macroscale immuno-magnetic setups utilizing test tube samples. Since magnetic field strength decays linearly with distance from the magnet, the low conduit height provides a functionally uniform magnetic field throughout the entire height of the conduit, which increases the efficiency of the capture. The low conduit height also keeps the sample extremely close to the magnet, which allows almost instantaneous immobilization and capture of tagged particles in flow.

In a second embodiment ("diverting"), as shown in FIG. 5, the magnetic conduit includes a first outlet 240 through which untagged particles flow to form a first group, and a second outlet 242a through which the magnetic field diverts a first portion of the tagged particles to form a second group. In the "diverting" embodiment, the magnetic conduit may include a third outlet 242b through which the magnetic field diverts a second portion of the tagged particles to form a third group, and similarly additional outlets to form additional groups. As shown in FIG. 6, the outlets may be located substantially at the same point along the magnetic conduit, and combination(s) of diamagnetic, paramagnetic, and ferromagnetic particles may be utilized to achieve simultaneous separation of multiple sample particle types by producing varying degrees of attracting or repelling forces on each individual particle type on the basis of the combination of particles binding to that particular particle type, as further described above. For instance, depending on the degree of attracting or repelling force produced on a given tagged particle, a given tagged particle may be directed specific distances toward or away from the magnetic field source towards specific outlets in order to achieve faster and more efficient, multi-level simultaneous particle separation. Alternatively, similar to the "capturing" embodiment, the "diverting" embodiment may include multiple stages or locations along the magnetic conduit where the various groups of particles are sequentially diverted out of a series of outlets. Furthermore, similar to the "capturing" embodiment, the "diverting" embodiment may include multiple tagging inlets for introducing multiple streams of tagging agent solution.

In one preferred embodiment depicted in FIG. 5, the magnetic conduit may include one or more buffer inlets for introducing a buffer stream 248. In these versions, the sample preferably flows into the magnetic conduit through a main sample inlet 211 and the buffer flows into the magnetic conduit through the buffer inlet 248. The buffer stream and sample stream do not mix due to laminar flow through the channel. As the sample flows through the conduit, tagged particles are preferably directed into the buffer stream by the magnetic field. In this embodiment, the magnetic force generated by the magnetic field is preferably strong enough to direct the tagged particles toward the buffer stream, but not strong enough to completely immobilize the tagged particles. The buffer stream preferably carries the tagged particles out through the outlet 242, which allows for continuous flow separation. This may be advantageous for increasing throughput in applications including isolating rare cells such as tumor cells, progenitor cells, and stem cells. The buffer is preferably similar to the sample in density, tonicity, charge, composition, and/or any property relevant to the application in order to reduce mixing and reduce the occurrence of other forces such as viscous and gravitational forces that compete with the magnetic force. However, the buffer may alternatively have a density, charge, chemical composition, biomolecular composition, and/or any suitable property that is different from the sample, such that any differences in properties may facilitate and/or enhance particle isolation. As an example, if the buffer includes a chemoattractant specific to attracting selected cells in the sample and if the buffer has a density lower than that of the sample, the differences between the buffer and the sample induce cell isolation by facilitating movement of cells in response to the chemoattractant. Furthermore, in this "diverting" embodiment, the magnetic conduit may include a slightly larger dimension along a direction in which tagged particles are diverted. Since magnetic field strength decays linearly with distance from the magnet, tagged cells in the buffer stream at a certain distance away from the magnet will levitate instead of being immobilized, and will be mobile enough to flow with the buffer stream.

Figure 17A:
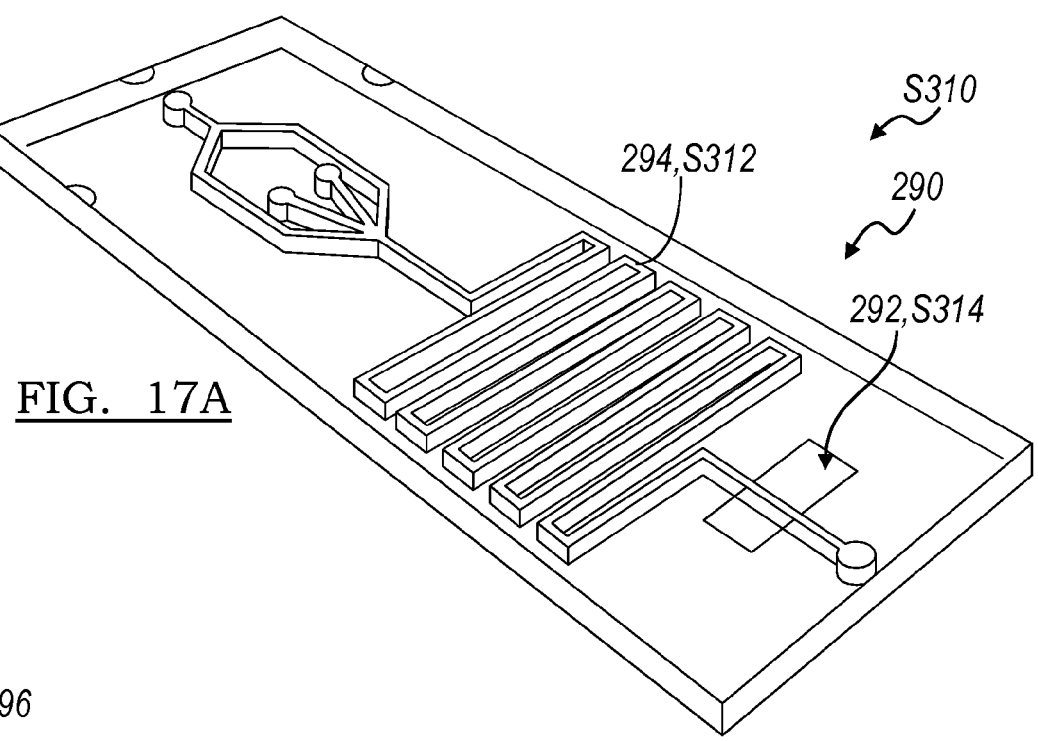
FIGS. 17A and 17B are schematics of the tagging agent removal module and tagging agent-tagging sponge interaction, respectively, of the system of a preferred embodiment.
Figure 17B:
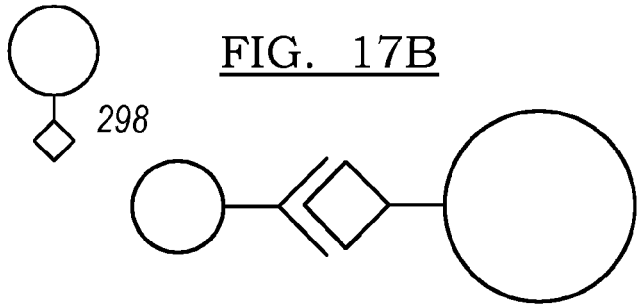

As shown in FIGS. 17-19, in some embodiments the system further includes a tagging agent removal module 290 and a detection apparatus 291. The tagging agent removal module 290 functions to separate unbound tagging agents 296 (free tagging agents not bound to sample particles) from the sample. The tagging agent removal module 290 is preferably similar to the tagging conduit except that the conduit 294 of the tagging agent removal module 290 facilitates the mixing of the sample with a solution of tagging sponges 298. As shown in FIG. 17B, the tagging sponges 298 are preferably specific to the functional end of the tagging agent, as further described above, such that the tagging sponge binds to the free tagging agents. The tagging agent removal module 290 preferably has an inlet for the sample and another inlet for a tagging sponge solution. As shown in FIG. 17A, the tagging agent removal module preferably include a magnetic field 292 that, as described above, interacts with the tagging agent-tagging sponge complexes to capture and/or deflect the tagging agent-tagging sponge complexes away from the sample, similar to the "capture" and "diverting" embodiments of the magnetic conduit.

Figure 19A:
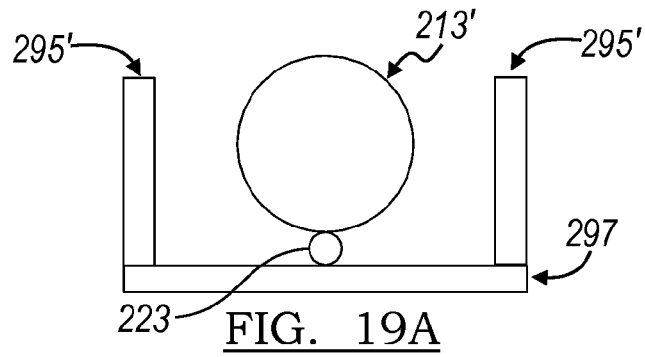
FIGS. 19A-19C are schematics of a preferred variation of the particle detection apparatus of the system of a preferred embodiment.
Figure 19B:
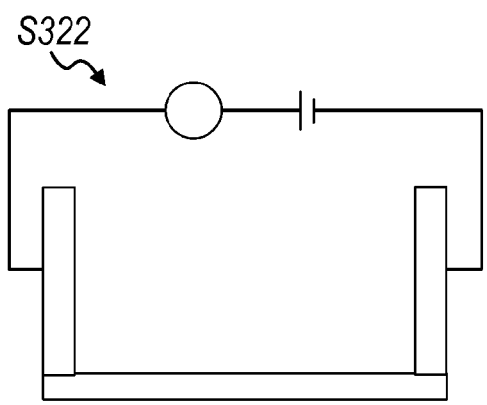
Figure 19C:
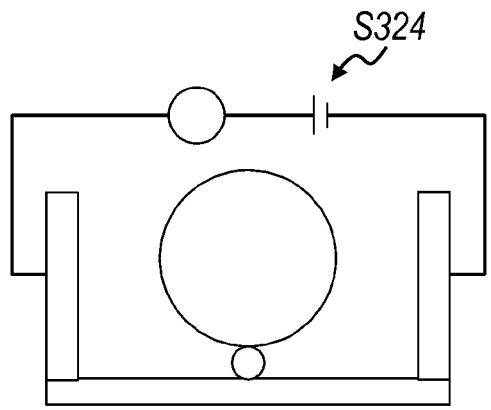

The detection apparatus 291 functions to enumerate particles in a sorted particle group of a sample particle type, such as for diagnostic or other analytical purposes. As shown in FIG. 18A, the detection apparatus 291 preferably includes a microfluidic channel 293 and a detector 295 that detects and enables enumeration of the particles. As shown in FIG. 19, the detector 295 preferably includes two electrodes 295', although alternatively the side walls or other surfaces of the microfluidic channel may integrally be an electrode. In the preferred embodiment, the floor of the microchannel 294 between the electrodes can be made of any surface that is unable to conduct current directly between the electrodes, such that current must pass through the fluid in the channel. Presence of sample particles in this fluid will characteristically alter the measured impedance, capacitance, resistance, and/or other suitable electrical characteristic within a circuit such as that depicted in FIG. 19. Detectable and quantifiable changes in these electrical measures can be utilized to determine the quantity of target complexes present as empirically determined for each particle application, as further described above. Additional labeling techniques using electrically active or inactive materials to further alter the impedance/capacitance and create unique stereotyped signatures can be utilized to augment this process and improve sensitivity. An alternative embodiment of the above electrode configuration would be to have the floor of the microchannel between the electrodes be made of any surface capable of conducting current directly between the electrodes, with an electromagnet 297 of some embodiment (similar to the magnetic conduit 230) underlying the floor used to bring the tagging agents 223 and their bound sample particles 213' into contact with the floor (FIG. 19A). Contact of the tagging agents 223 with the floor and presence of their bound particle 213' between the electrodes 295' alters the measured impedance, capacitance, resistance, and/or other suitable electrical characteristic within the circuit. Detectable and quantifiable changes in these electrical measures can be utilized to determine the quantity of target complexes present. Additional labeling techniques using electrically active or inactive materials to further alter the electrical measures of the circuits can be utilized to augment this process and improve sensitivity.

As shown generally in FIG. 18B, the detection apparatus 291 may additionally and/or alternatively include other kinds of detectors 295 on a microfluidic chip and cooperate with labeling reagents or tags 299 for 1) electrochemical detection, 2) fluorescence-based detection, 3) surface enhanced Raman scattering (SERS), and/or 4) thermal detection, which are known to one skilled in the art, or any suitable detection methods. The detector 295 preferably receives quantifiable data on one or more physical parameters of an interaction (e.g., electric, fluorescent, magnetic, chemical interactions) between tagged particles and the labeling reagent. This reading could be processed by a biorecognition microprocessor to determine presence, absence, or overall quantity of particles in the fluid at the detector site based on empirically established parameters.

In a first alternative, the electrochemical technique relies on attachment of electrochemical tags to the tagging agent-sample particle complex and typically involves 3 electrodes with the additional electrode serving as the reference electrode. The presence of the electrochemical tag induces either oxidation or reduction at the sample electrode altering the current or voltage within the circuit. The degree of alteration can then be correlated to the amount of tag present, which will directly relate to the amount of bound target particle present. In a second alternative, the fluorescent-based detection involves the attachment of fluorescent tags to the tagging agent-sample particle complex. Light source for excitation (e.g. LEDs) and detectors (photodiodes) can be integrated on chip to detect total fluorescence, which correlates to the amount of tag present, which directly correlates to the amount of bound target particle present. In a third alternative, the SERS technique involves the attachment of nanoparticles to the bead complex. Raman scattering (at frequencies different from excitation source) can be enhanced and detected. SERS is an alternative to fluorescence-based detection and does not require fluorescent tags which may degrade over time. In a fourth alternative, thermal detection utilizes nanoparticles like gold nanoshells, which at certain wavelengths of excitation produce heat. Thermal detection can be used to correlate amount of heat produced to amount of tag present, which directly correlates to the amount of bound target particle present.

Figure 20:
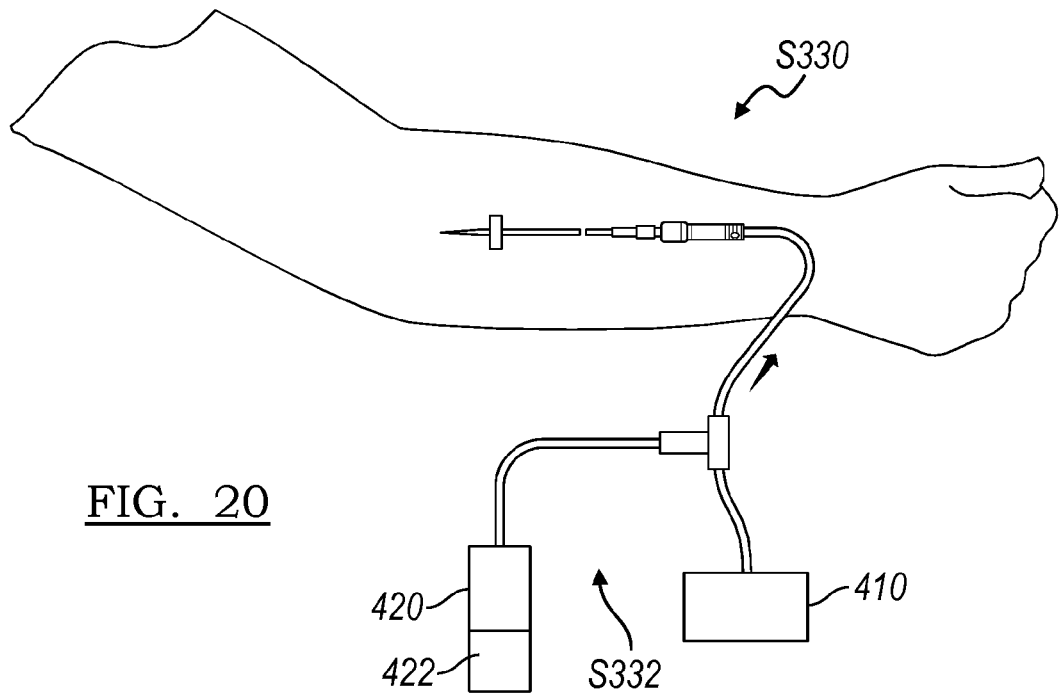
FIG. 20 is a schematic of the recirculation module and therapeutic agent reservoir of the system of a preferred embodiment.

In some embodiments, as shown in FIG. 20, the system further includes a recirculation module 410 that recirculates at least a portion of the sample back through the body of the patient, and may further include one or more reservoirs 420 from which a therapeutic agent 422 such as a drug or nutrient is added to the recirculating portion of the sample or otherwise administered directly to the patient. Various actions of the system 200, particularly those of the recirculation module 410 and withdrawal from the reservoir 420, can be controlled electronically by a microprocessor in response to the results of the sample particle detection and enumeration. The recirculating module preferably returns the sample portion to the body of the patient through a catheter, which may be the sampling catheter 212 or another suitable cannula coupled to the patient. The decision of the microprocessor to recirculate a portion of the sample and the amount of the therapeutic agent added to the returning sample portion may supplement an existing patient treatment, and/or may be affected by enumeration data obtained with the particle detection apparatus. The addition of the recirculation module enables 1) targeted removal of particles not just nonspecific filtering and 2) targeted amount of particle removal, such as by recirculation of portions based on enumeration to meet programmable parameters. In this way, the recirculation module preferably enables a kind of programmable dialysis customizable to the needs of the patient.

In some embodiments of the system, the system further includes a lytic conduit 250 that selectively destroys certain unwanted particles by lysis. The lytic conduit preferably processes the sample prior to the tagging conduit and/or magnetic conduit, to reduce or eliminate common or plentiful untargeted particles upfront and thereby increasing the relative presence of ordinarily rarer target cells and improving efficiency of the system. Alternatively, the lytic conduit may be utilized after the tagging and magnetic conduits, or in any suitable order. The lytic conduit exploits the differences in osmotic resistances of different cells to cause selective lysis of certain particle types by exposing the sample to hypotonic and/or hypertonic solutions of lytic agents in a controlled manner. In one example embodiment, the lytic conduit encourages high speed (preferably on the order of less than 0.5 seconds) and high efficiency mixing of the sample 211 and a lytic solution 260. As shown in FIG. 12, the lytic conduit is preferably is similar in structure to the tagging conduit, except for the following differences. The lytic conduit preferably has a second inlet 254, in addition to the sample inlet 252, used to introduce the lytic solution into the lytic conduit. The lytic solution 260 used in the cell depletion microfluidic device depends on the osmotic resistances of the cells to be depleted in the sample, and the osmotic resistances of the other cells in the sample. Similar to the flow rates in the tagging conduit, the relative flow rates of the sample and lytic solution are preferably adjustable to optimize turbulent mixing and create pre-determined relative concentrations of particles in the sample and the solutes in the lytic solution. The flow rates are also preferably adjustable to expose the sample to the lytic solution for an appropriate amount of time for high speed and high efficiency. Exposure time can be varied from 5 seconds to several minutes, depending on the application, and the flow through the device preferably ensures that every particle in the sample experiences the same conditions, to increase consistency. The lytic conduit preferably further includes at least one buffer inlet 256, located near the end of the lytic conduit, that is used to introduce a neutralizing buffer such as saline of an appropriate salt concentration that returns the sample to isotonic conditions. The location of the buffer inlet and the flow rate of the neutralizing buffer are preferably selected and/or adjusted to further control the amount of time the sample is exposed to the lytic agent. The lytic conduit is preferably manufactured with conventional soft lithography techniques similar to the tagging conduit, but may be manufactured with any suitable technique. As the use of lysis solutions for depleting cells in a fluid are known in the art, similar versions of the described lytic conduit may additionally and/or alternatively be used in the system.

Figure 13:
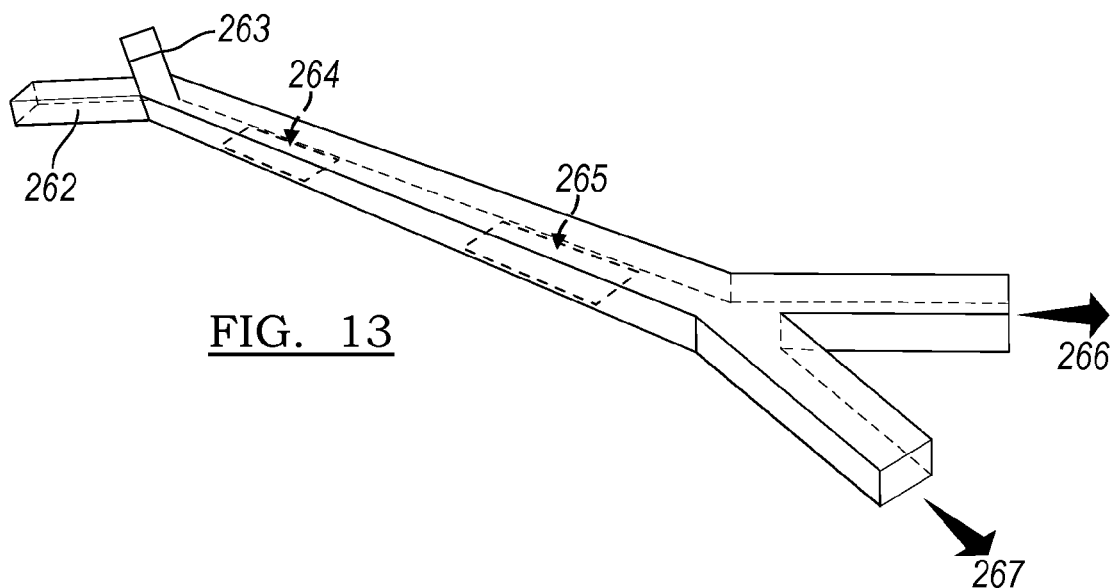
FIGS. 13 and 14 are a perspective schematic view and flowchart for operation, respectively, of a conduit for sorting intracellular particles.
Figure 14A:
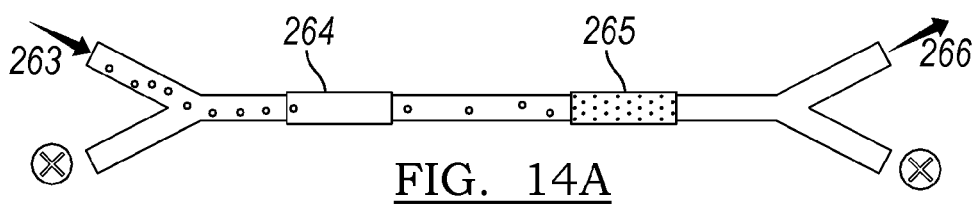
Figure 14B:
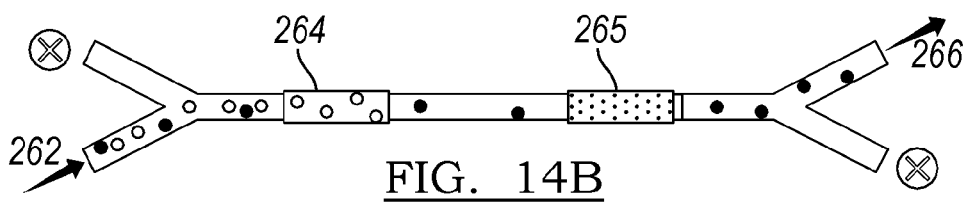
Figure 14C:
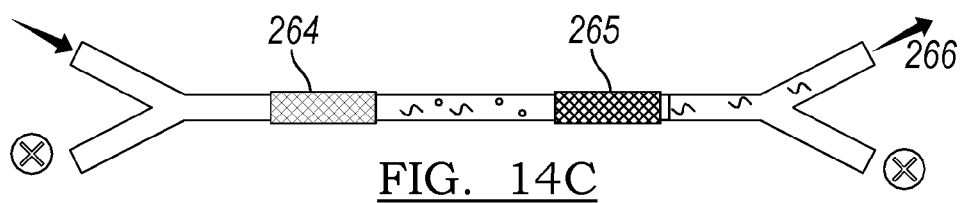
Figure 14D:
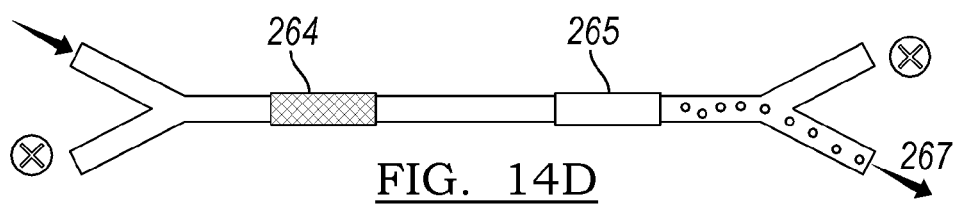

Furthermore, lysis can be used to release intracellular particles for subsequent tagging and sorting. As shown in FIG. 13, a conduit combining aspects of the magnetic and lytic conduit for sorting intracellular particles includes two inlets, two capture regions, and two outlets. A solution containing magnetic beads specific to intracellular contents enters the conduit through one inlet 263 or another inlet and the second magnetic capture region 265 captures these intracellular-designated beads (FIG. 14A). The sample or presorted cellular subpopulations in the sample including tagged particles enters the conduit through one inlet 262 and the first magnetic capture region 264 captures tagged cells in the sample (FIG. 14B). A lytic solution enters the conduit through one of the inlets and lyses the captured cells in the first magnetic capture region, thereby releasing intracellular conduits to flow through the conduit and bind to captured intracellular-designated beads in the second magnetic capture region and allowing cell debris to pass through a waste outlet (FIG. 14C). The intracellular particles are released from the second magnetic capture region and flow through a second outlet for collection and/or analysis (FIG. 14D). The intracellular particle release can be performed in one or more different ways, including: demagnetizing the second magnetic capture region and adding an elution buffer to wash the intracellular particles through the second outlet, or adding a reagent through one of the inlets to release the intracellular particles from the beads. Furthermore, sorting and isolation of intracellular particles may include one or more of the "capture" or "diverting" embodiments of the magnetic conduit in any combination or permutation of the system and methods for sorting particles, as described above. In this way, multiple intracellular components can by rapidly processed in much the same way as extracellular components.

In some embodiments of the system, the system further includes an immunoaffinity capture chamber lined with capture particles (such as antibodies or antibody mimetics) that selectively bind to and capture at least one of the sample particle types. Similar to the lytic depletion module, the immunoaffinity capture chamber is preferably utilized prior to the tagging and/or magnetic conduits for improved efficiency. The immunoaffinity capture chamber may additionally and/or alternatively be utilized in any relative order; for example, after the magnetic conduit as an additional sorting step. As shown in FIG. 15, the immunoaffinity capture chamber preferably includes a surface 272, preferably a bottom surface, having immobilized capture particles 274 such as antibodies or antibody mimetics. As the sample flows through the immunoaffinity capture chamber, cells or other particles specific to the immobilized capture particles preferably bind to the surface of the capture chamber, allowing other particles to remain unbound and uncaptured. The capture chamber may incorporate features such as herringbone ridges or transverse posts to induce chaotic sample flow, thereby increasing the likelihood of binding interactions for particle depletion, or may incorporate pulsatile flow and/or an incubation period during which flow ceases and sample particles sediment to the bottom surface for selective binding and immobilization. Following immobilization of the captured particles, a buffer fluid may be introduced as a secondary wash to flush captured particles out of the capture chamber. The capture chamber may be used for positive selection or negative selection of sample particles. Such immunoaffinity capture chambers are known in the art, and any suitable immunoaffinity capture chamber may additionally and/or alternatively be used.

In some embodiments, the system further includes a fixation and permeabilization module, which functions to enable tagging of intracellular contents in the sample. As shown in FIG. 16, the fixation and permeabilization module preferably includes two microfluidic channels fluidly connected in series, which are preferably similar to the tagging and lytic conduits in that they preferably include textured surfaces and/or are in a serpentine shape to induce chaotic mixing and are manufactured similar to the tagging and lytic conduits. In the first microfluidic channel 280, the sample 211 is preferably mixed with a fixation solution 284 such as paraformaldehyde or other suitable fluid, to rigidify cell membranes. In the second microfluidic channel, the sample is preferably mixed with a permeabilization soluton 286 such as methanol or another suitable fluid, to permeate the cell membrane and allow tagging agents access intracellular contents for selective binding in the tagging conduit. This module preferably processes the sample before the tagging conduit, but may process a presorted group of particles before a secondary processing in another tagging conduit, enabling sorting based on extracellular and intracellular particles in two successive sorting stages, respectively. As one illustrative example of sorting on the basis of both intracellular and extracellular targets, the percentage of activated T-cells in a sample can be determined by sorting out T-cells having phosphorylated signaling molecules specific to cell activation. A first sorting stage may involve tagging functionalized, immuno-magnetic beads specific to a cell surface receptor such as CD4 to sort and isolate a group of T-cells from a blood sample. The group of T-cells can then be passed through the fixation and permeabilization module to allow access of tagging agents to intracellular contents. The group of T-cells may then be mixed with a tagging agent solution containing paramagnetic beads coupled to antibodies specific to phosphorylated-STAT proteins, which bind to activated T-cells (STAT phosphorylation is associated with induction of cytokine gene expression consistent with T-cell activation). In a second sorting stage, the activated, tagged T-cell subset is pulled more toward the magnet than the unactivated T-cell subset due to the presence of the intracellular paramagnetic tag(s), thereby separating the activated T-cells, such as for enumeration and/or other analysis.

Although each of the method and system is preferably one or more of the described variations, additional embodiments of the method and system include every combination and permutation of the various steps and devices. Furthermore, additional embodiments include those having multiple instances of any of the steps and/or devices.

3. Examples

In a first example, the system is used to separate three immune lineages from a sample. A blood sample is mixed with a solution containing 1) small diamagnetic beads coupled to an anti-CD3 antibody and (2) small paramagnetic beads coupled to an anti-C20 antibody. The sample-solution mixture is passed through a mixing channel with herringbone ridges that induces chaotic mixing with the sample to increase binding efficiency between the beads and specific sample cells. The sample is then passed through a "deflection"-based magnetic sorting chamber having a magnet, in which CD3+ T-cell lymphocytes are deflected away from the magnet into Output Stream 1 and CD20+ B-cell lymphocytes are attracted toward the magnet and pulled into Output Stream 3. The remaining unbound sample passes through into Output Stream 2.

The sample portion from Output Stream 1 is then mixed with a solution containing 1) large diamagnetic beads coupled to an anti-CD4 antibody and 2) large paramagnetic beads coupled to an anti-CD8 antibody. The sample-solution mixture is again passed through a mixing channel with herringbone ridges to increase binding efficiency. The large beads dominate and reduce the effect of the previously bound, smaller anti-CD3 beads. Alternatively, Output Stream 1 can be pre-washed with an appropriate reagent to cause unbinding and removal of the anti-CD3 beads. The sample is then passed again through a "deflection"-based magnetic sorting chamber, in which CD3+CD4+ helper T-cell lymphocytes are deflected away from the magnet into Output Stream 1.1 and CD3+CD8+ cytotoxic T-cells are attracted toward the magnet and pulled into Output Stream 1.3. The remaining unbound sample passes through Output Stream 1.2. In this manner, a complex solution of blood is separated into 3 key immune lineages: B Cells (Output Stream 3), T helper cells (Output Stream 1.1) and cytotoxic T-cells (Output Stream 1.3).

In a second example, peripheral blood endothelial progenitor cells (PBEPCs), which are of the hemangioblast phenotype expressing CD34+CD133+CD45−, are separated from a sample as one example of stem cell isolation from peripheral blood. A blood sample is passed through a lytic conduit that mixes the sample with a stream of deionized water, which lyses erythrocytes while preserving all other nucleated cell types. The sample is then passed through an immunoaffinity chamber lined with anti-CD45 antibodies that bind to CD45+ cells, thereby depleting the sample of CD45+ cells. The rest of the sample is mixed with a solution containing diamagnetic magnetic beads specific to CD34 in a mixing channel having herringbone ridges for increased binding efficiency, and subsequently passed through a magnetic sorting chamber that captures the magnetic beads, thereby capturing CD34+ cells. After the unbound portion of the sample exits the magnetic sorting chamber, the magnet is deactivated and releases captured CD33+ cell with into a buffer solution. In a final sorting stage, the released cells are passed into an immunoaffinity chamber lined with anti-CD133 antibodies that capture CD34+ cells that are also CD133+. The cells captured in this final sorting stage are the sorted PBEPCs, or CD45−CD133+CD34+ cells.

As a person skilled in the art will recognize from the previous detailed description and from the figures and claims, modifications and changes can be made to the preferred embodiments of the invention without departing from the scope of this invention defined in the following claims.

We claim:

1. A microfluidic system for isolating particles from biological fluid of a patient, comprising:
    a sampling module including a cannula coupled to the patient that obtains a sample of biological fluid from the patient, wherein the sample contains particles of multiple sample particle types;
    a microfluidic tagging conduit, fluidly coupled to the sampling module at a point-of-care of the patient, having:
        a first inlet that receives the sample;
        a second inlet that receives a solution comprising a magnetic tagging agent, wherein the magnetic tagging agent selectively binds to and tags particles of at least one particle type of the multiple sample particle types; and
        a textured surface that induces turbulent mixing of the particles with the magnetic tagging agent, thus producing a set of tagged particles; and
    a microfluidic magnetic conduit, fluidly coupled to the microfluidic tagging conduit and having at least one magnet providing a magnetic field that interacts with the set of tagged particles, such that the particles in the sample are sorted into at least two groups based on an interaction between the set of tagged particles and the magnetic field, wherein the microfluidic magnetic conduit includes a serpentine-shaped sorting region including a first surface configured to immobilize a first portion of the set of tagged sample particles by the magnetic field and allow passage of a set of untagged sample particles, and a second surface configured to immobilize a second portion of the set of tagged sample particles by the magnetic field and allow passage of the set of untagged sample particles, wherein the first surface and the second surface are coupled by a channel not within the magnetic field, that angularly displaces flow passing the first surface toward the second surface.

2. The system of claim 1, wherein the textured surface of the tagging conduit includes herringbone structures.

3. The system of claim 1, wherein the magnetic conduit includes a first outlet through which untagged particles flow to form a first group, and a surface, onto which the magnetic field captures at least a portion of the tagged particles to form a second group.

4. The system of claim 3, wherein the magnetic conduit includes a second surface onto which the magnetic field captures a second portion of the tagged particles to form a third group.

5. The system of claim 4, wherein the second surface is downstream of the first surface in the magnetic conduit.

6. The system of claim 1, wherein the microfluidic magnetic conduit includes a first outlet through which the set of untagged particles flow to form a first group, and a second outlet through which the the set of tagged particles is diverted to form a second group.

7. The system of claim 6, wherein the second outlet is downstream of the first outlet.

8. A microfluidic system for isolating particles from a sample of biological fluid of a patient comprising sample particles of interest, the microfluidic system comprising:
   a sampling module comprising a tubing that is configured to couple, at a point-of-care of the patient, to a cannula that obtains the sample of biological fluid from the patient;
   a microfluidic tagging conduit, comprising:
      a first inlet region configured to fluidically couple to the tubing of the sampling module to receive the sample,
      a second inlet region configured to receive a solution of a magnetic tagging agent that selectively binds to and tags sample particles of interest, and configured to merge the magnetic tagging agent into the sample,
      a serpentine-shaped mixing region comprising a textured surface configured to induce turbulent mixing of the sample and the magnetic tagging agent, creating an unsorted mixture comprising a set of tagged sample particles and a set of untagged sample particles;
   a microfluidic magnetic conduit configured to fluidically couple to the serpentine-shaped mixing region, the microfluidic magnetic conduit comprising a magnetic conduit inlet configured to receive the unsorted mixture, a first magnetic conduit outlet, and a second magnetic conduit outlet; and
   a magnet providing a magnetic field at the microfluidic magnetic conduit, wherein the magnetic field is configured to:
      allow the set of untagged sample particles to flow through the first magnetic conduit outlet, thereby forming a first group of sample particles and
      allow flow of the set of tagged sample particles through the second magnetic conduit outlet based on an interaction between the magnetic field and the set of tagged sample particles, thereby forming a second group of sample particles; and
   wherein the microfluidic magnetic conduit includes a serpentine-shaped sorting region including a first surface configured to immobilize a first portion of the set of tagged sample particles by the magnetic field and allow passage of a set of untagged sample particles, and a second surface configured to immobilize a second portion of the set of tagged sample particles by the magnetic field and allow passage of the set of untagged sample particles, wherein the first surface and the second surface are coupled by a channel not within the magnetic field, that angularly displaces flow passing the first surface toward the second surface.

9. The system of claim 8, wherein the tubing of the sampling module is configured to couple to a catheter inserted in the patient at the point-of-care.

10. The system of claim 8 further comprising a perturbing mechanism configured to be coupled to the sampling module.

11. The system of claim 10, wherein the perturbing mechanism comprises a rocker.

12. The system of claim 8, wherein a portion of the second inlet region is configured to divide and flank a portion of the first inlet region.

13. The system of claim 8, wherein the microfluidic magnetic conduit is further configured to couple to a buffer inlet for introducing a buffer stream, wherein the magnetic field is configured to divert flow of the set of tagged sample particles into the buffer solution and through the second magnetic conduit outlet, in a continuous flow separation.

14. The system of claim 8, wherein the microfluidic magnetic conduit further comprises a third magnetic conduit outlet.

15. The system of claim 14, wherein the magnetic field is configured to divert flow of a second set of tagged sample particles through the third magnetic conduit outlet, thereby forming a third group of sample particles.

16. The system of claim 14, wherein the microfluidic magnetic conduit comprises a first branch terminating in the first magnetic conduit outlet, a second branch terminating in the second magnetic conduit outlet, and a third branch terminating in the third magnetic conduit outlet.

17. The system of claim 16, wherein the first, second, and third branches are located at substantially the same longitudinal point along the length of the microfluidic magnetic conduit.

18. The system of claim 8, wherein the magnet is an electromagnet.

19. The system of claim 8, wherein the microfluidic magnetic conduit is further configured to be fluidically coupled to a second magnetic tagging solution inlet, downstream of the second surface, and configured to receive a second solution of magnetic tagging agents that selectively bind to and tag other sample particles of interest.

20. The system of claim 8, further comprising detection apparatus configured to enumerate particles in at least one of the first group of sample particles and the second group of sample particles.

21. The system of claim 20, wherein the detection apparatus measures an electrical parameter that is altered by the presence of at least one particle of the first group of sample particles and the second group of sample particles.

* * * * *